US011219743B2

(12) United States Patent
Freeseman et al.

(10) Patent No.: US 11,219,743 B2
(45) Date of Patent: Jan. 11, 2022

(54) PUNCTURE DEVICES, AND SYSTEMS AND METHODS FOR ACCESSING TISSUE

(71) Applicant: Boston Scientific Scimed, Inc., Maple Grove, MN (US)

(72) Inventors: Lance A. Freeseman, Greenfield, MN (US); James P. Rohl, Prescott, WI (US); Joel T. Eggert, Plymouth, MN (US); Eric M. Petersen, Maple Grove, MN (US); Craig M. Wilson, Minneapolis, MN (US); Douglas D. Pagoria, Evergreen, CO (US); Todd College, Little Canada, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 277 days.

(21) Appl. No.: 16/279,536

(22) Filed: Feb. 19, 2019

(65) Prior Publication Data
US 2019/0255285 A1   Aug. 22, 2019

Related U.S. Application Data

(60) Provisional application No. 62/632,854, filed on Feb. 20, 2018.

(51) Int. Cl.
*A61M 25/00* (2006.01)
*A61B 17/34* (2006.01)
(Continued)

(52) U.S. Cl.
CPC ..... *A61M 25/0084* (2013.01); *A61B 17/3478* (2013.01); *A61B 17/3496* (2013.01);
(Continued)

(58) Field of Classification Search
CPC ............ A61B 17/3478; A61B 17/3494; A61B 17/347; A61B 2017/00367; A61B 2017/3425; A61M 2025/0089
See application file for complete search history.

(56) References Cited

U.S. PATENT DOCUMENTS 4,609,370 A * 9/1986 Morrison ........... A61B 17/3401
600/567
5,171,245 A * 12/1992 Cezana ............. A61B 17/3417
606/53
(Continued)

FOREIGN PATENT DOCUMENTS

EP         2662107 A2    11/2013
WO    2010078196 A1     7/2010

OTHER PUBLICATIONS

International Search Report and Written Opinion for International application No. PCT/US2019/018564, dated May 23, 2019, 11 pages.
(Continued)

*Primary Examiner* — Alexander J Orkin

(57) ABSTRACT

Tissue puncture devices, and systems and methods for accessing tissue (e.g., cardiovascular tissue) according to the present disclosure may include a tubular sheath extending along a longitudinal axis, the tubular sheath having a proximal end and a distal end, a needle disposed coaxially in the sheath, the needle having a proximal end and a distal end and being movable along the longitudinal axis of sheath, and a needle control mechanism disposed at the proximal end of the needle, the needle control mechanism being configured to lock the distal end of the needle in a first position retracted within the distal end of the sheath, and release the needle to an unlocked second position such that the distal end of the needle is extendable beyond the distal end of the sheath.

20 Claims, 18 Drawing Sheets

(51) Int. Cl.
*A61B 17/00* (2006.01)
*A61M 25/09* (2006.01)

(52) U.S. Cl.
CPC .................. *A61M 25/0074* (2013.01); *A61B 2017/00247* (2013.01); *A61B 2017/00367* (2013.01); *A61B 2017/3425* (2013.01); *A61M 25/0068* (2013.01); *A61M 25/09* (2013.01); *A61M 2025/0089* (2013.01); *A61M 2025/0095* (2013.01)

(56) References Cited

U.S. PATENT DOCUMENTS

| | | | | |
|---|---|---|---|---|
| 5,242,427 A * | 9/1993 | Bilweis | ................. | A61B 17/34 604/164.11 |
| 5,425,718 A * | 6/1995 | Tay | ................. | A61M 25/0643 604/158 |
| 5,645,076 A * | 7/1997 | Yoon | ................. | A61B 17/3417 600/567 |
| 6,066,146 A * | 5/2000 | Carroll | ............... | A61B 17/0401 606/144 |
| 6,554,794 B1 * | 4/2003 | Mueller | ............. | A61B 17/3478 604/528 |
| 2005/0043682 A1 * | 2/2005 | Kucklick | ........... | A61M 3/0279 604/164.09 |
| 2006/0276749 A1 * | 12/2006 | Selmon | .................... | A61B 6/12 604/164.01 |
| 2007/0270751 A1 * | 11/2007 | Stangenes | ........ | A61B 17/00234 604/164.1 |
| 2009/0030380 A1 * | 1/2009 | Binmoeller | ......... | A61M 25/104 604/264 |
| 2010/0016878 A1 * | 1/2010 | Smith | ................ | A61B 17/3417 606/185 |
| 2013/0345765 A1 * | 12/2013 | Brockman | ............ | A61B 17/1642 606/86 R |
| 2016/0361088 A1 * | 12/2016 | Maguire | ............... | A61F 2/962 |
| 2017/0020567 A1 | 1/2017 | Hassett | | |

OTHER PUBLICATIONS

Author unknown, "Trans-Septal Puncture Procedures and Devices", DocPlayer [online] date unknown [retrieved on Aug. 16, 2019]. Retrieved from Internet URL: https://docplayer.net/21784640-Trans-septal-puncture-procedures-and-devices.html, 4 pages.

* cited by examiner

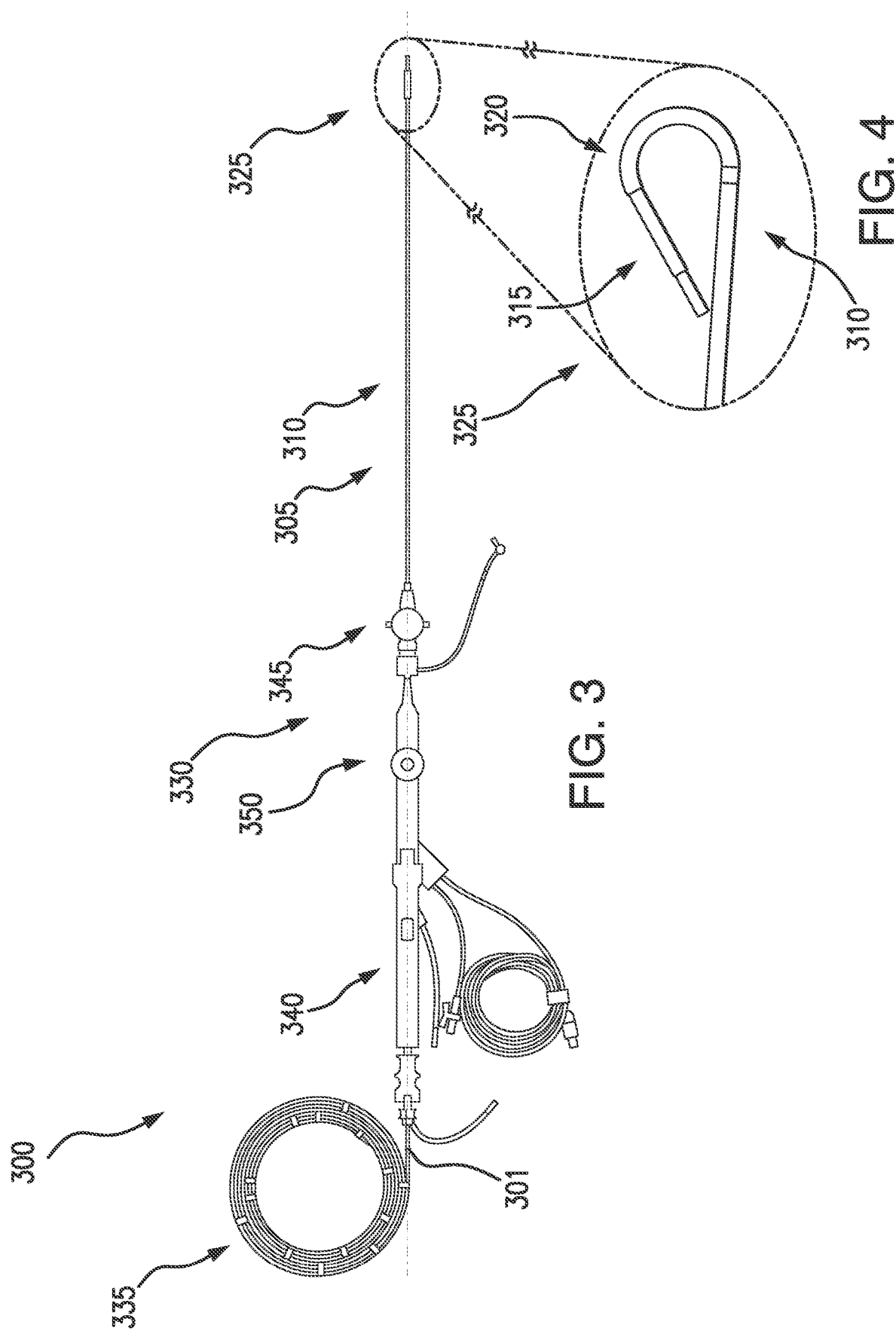

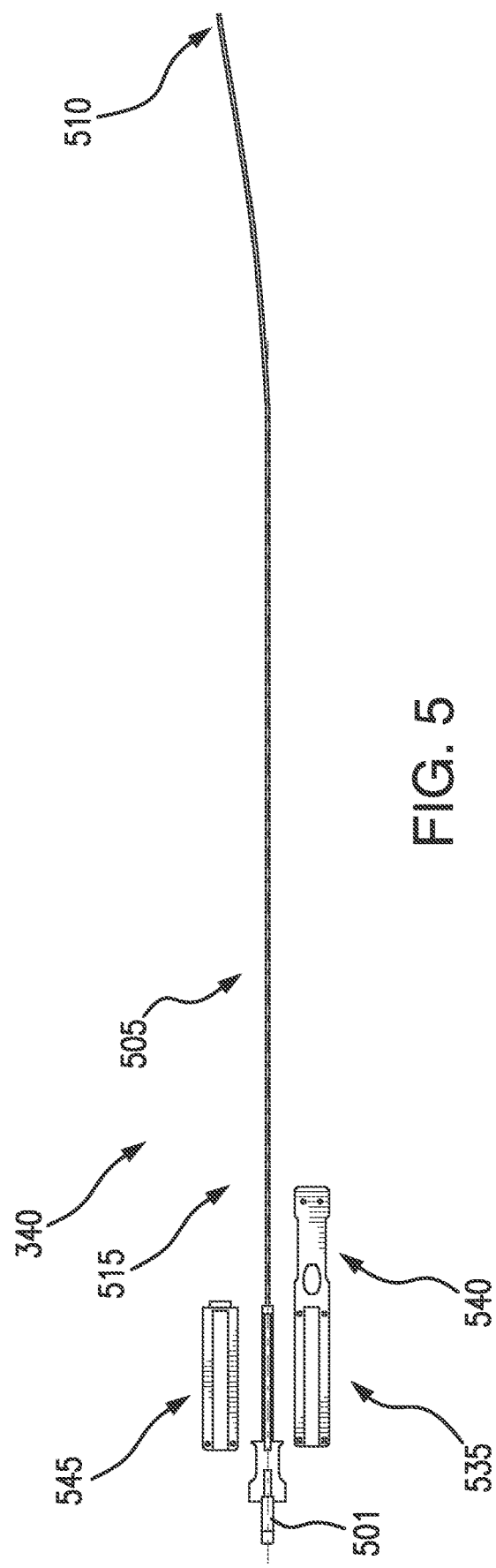

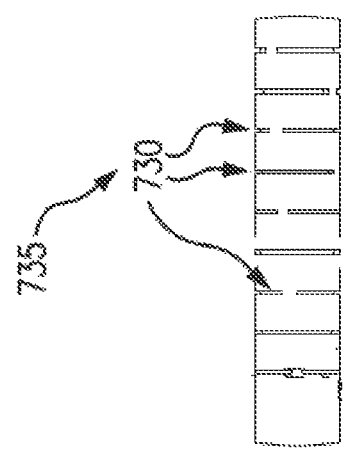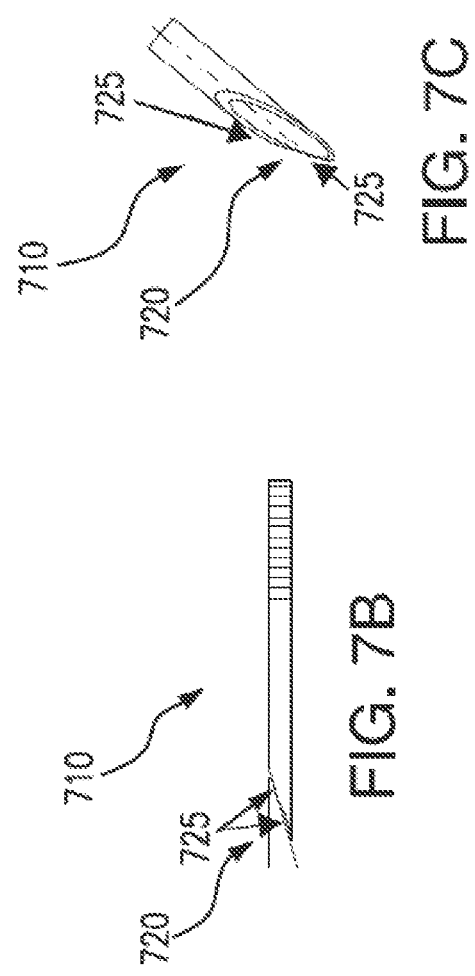

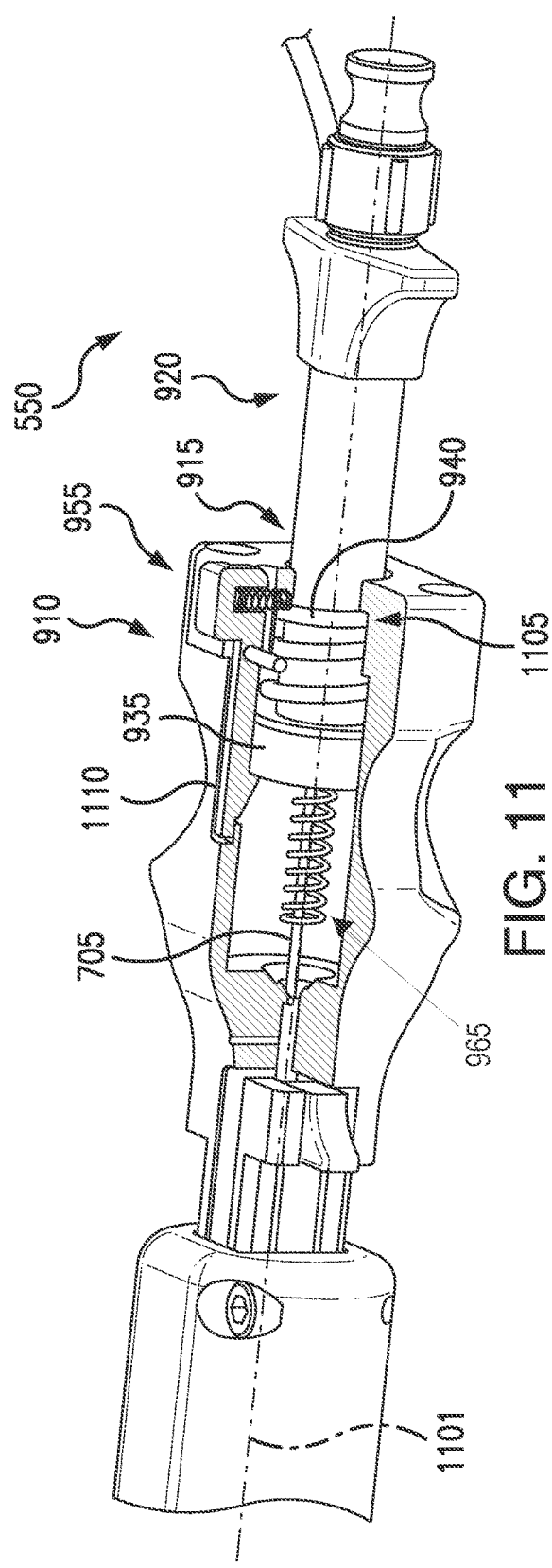
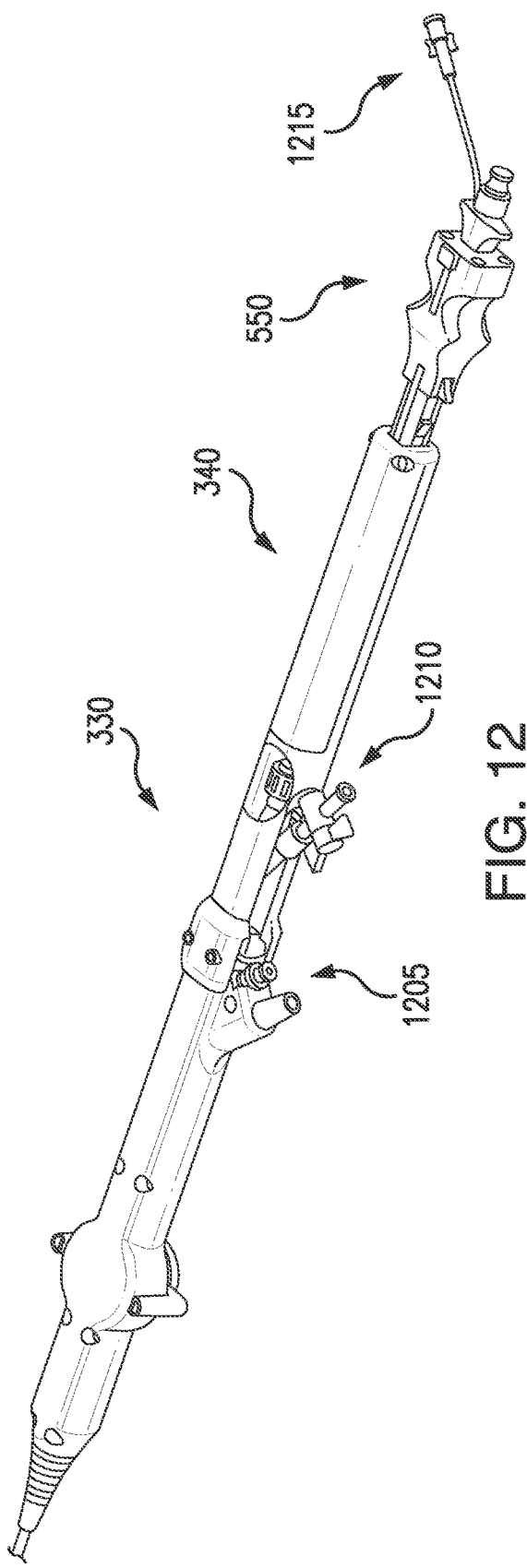
FIG. 11
FIG. 12

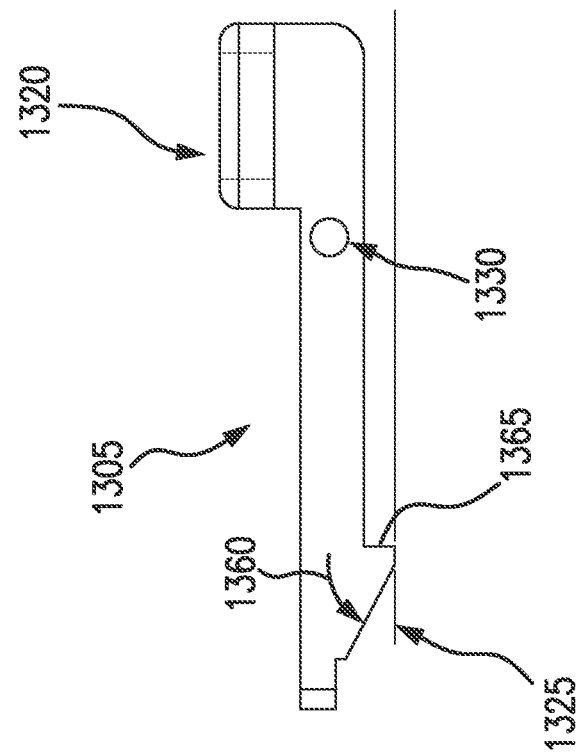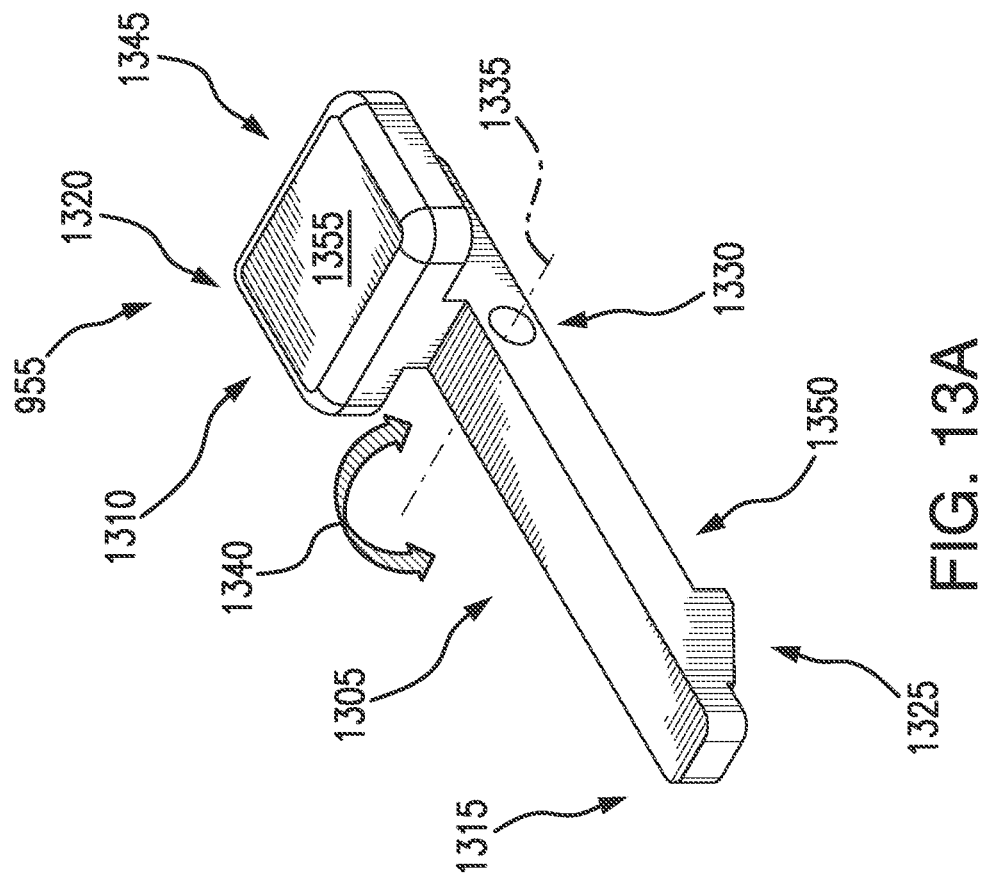

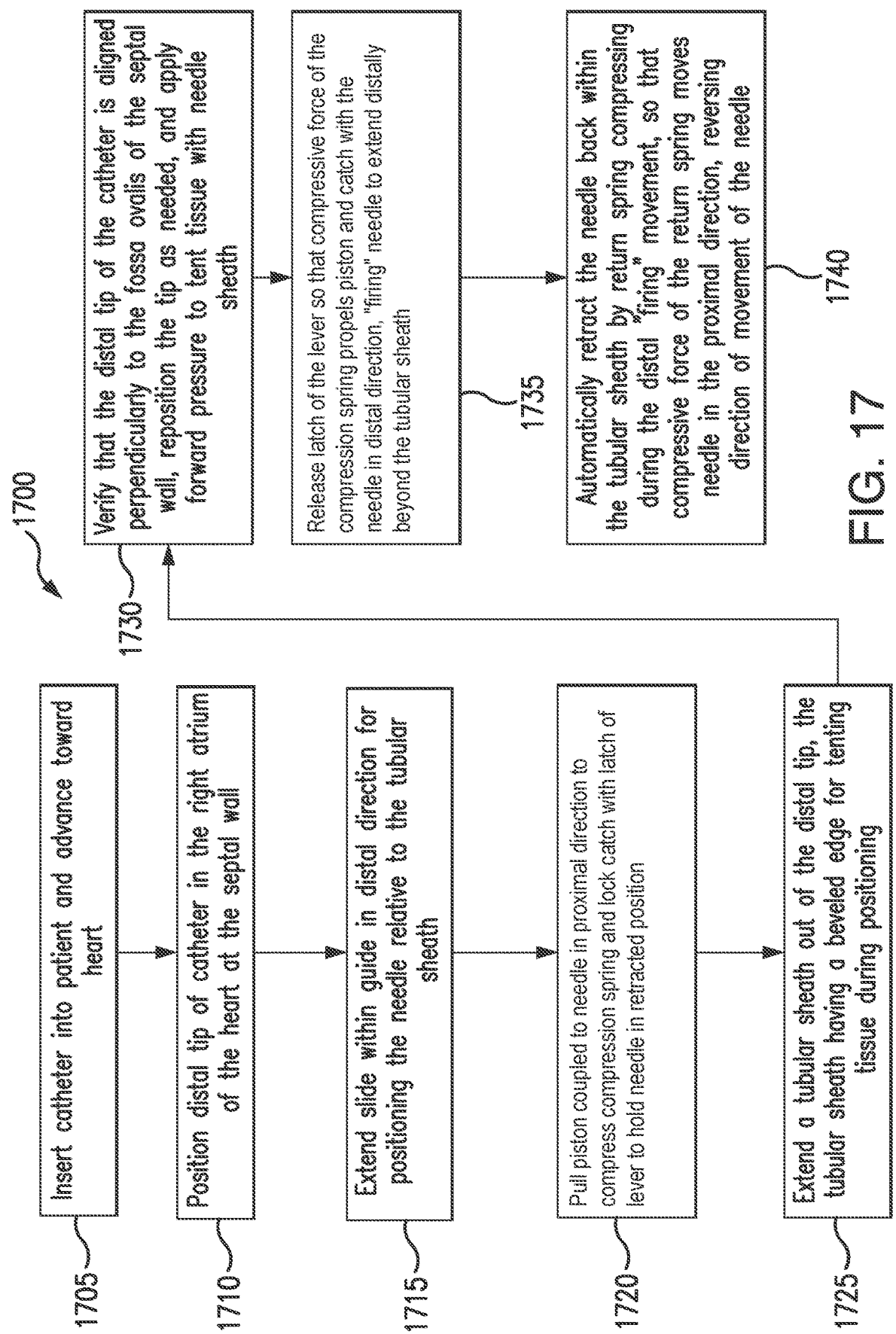

PUNCTURE DEVICES, AND SYSTEMS AND METHODS FOR ACCESSING TISSUE

CROSS-REFERENCE TO RELATED APPLICATIONS

This application is a non-provisional application of, and claims the benefit of priority to, U.S. Provisional Application Ser. No. 62/632,854, filed Feb. 20, 2018, entitled "Puncture Devices and Systems and Methods for Accessing Tissue," the entirety of which application is expressly incorporated by reference herein.

FIELD

The present disclosure relates generally to access devices in tissue, and, more particularly, to puncture devices and systems and methods for accessing tissue (e.g., cardiovascular tissue).

BACKGROUND

Access devices, as described for example in the context of cardiovascular device, may be used to access a patient's heart so that additional therapies, such as atrial fibrillation ablation (e.g., electroporation), treatment of structural heart disease (e.g., valve repair), and the like, may be delivered to the patient. These treatments may require access to the left atrium of the heart, so that a trans-septal procedure (e.g., crossing the septal wall that separates the right atrium and the left atrium) may be performed by a medical professional before performing additional cardiovascular therapies.

It may be desirable for the trans-septal procedure to occur at the fossa ovalis, an area of the septal wall having a thinner tissue wall than another portion of the septal wall, so that a device may more easily pierce through the tissue. Typically, devices may be navigated by fluoroscopy and/or intracardiac echo. However, current cardiovascular access devices may be unable to be accurately located with the fossa ovalis at the septal wall and/or may be unable to be accurately oriented with the septal wall for efficient access. Additionally, current devices, which may utilize needles, guidewires, and/or radio frequency (RF) energy, may suffer from an inability to adequately prevent against damaging veins, surrounding heart tissue, and/or the pericardium.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, a tissue puncture device for accessing tissue (e.g., cardiovascular tissue) may include a tubular sheath extending along a longitudinal axis, and the tubular sheath may have a proximal end and a distal end. A needle may be disposed coaxially in the sheath, and the needle may have a proximal end and a distal end and may be movable along the longitudinal axis of sheath. A needle control mechanism may be configured to lock the distal end of the needle in a first position retracted within the distal end of the sheath, and an unlocked second position such that the distal end of the needle is extendable beyond the distal end of the sheath.

According to an exemplary embodiment of the present disclosure, a method for accessing tissue may include positioning a distal tip of a catheter for a needle deployment device including a needle to access selected tissue. A needle control mechanism may be set in a retracted position. The needle control mechanism may be locked in the retracted position. The needle may be deployed to access the selected tissue by releasing the locked needle control mechanism. The needle may extend distally beyond the distal tip of the catheter.

In various of the foregoing and other embodiments of the present disclosure, the needle control mechanism may include a needle deployment device disposed at a proximal end of the needle control mechanism, and the needle deployment device may have a body portion couplable to a cover portion. The needle deployment device may include a piston disposed within an aperture of the cover portion such that a proximal end of the piston is external to the cover portion and the body portion and a distal end of the piston is internal to the cover portion and the body portion. The distal end of the piston may be coupled to the proximal end of the needle, and the piston may be movable relative to the cover portion along the longitudinal axis of the sheath. The needle deployment device may further include: a catch coupled to the distal end of the piston; a compression spring extending along the piston and disposed between the cover portion of the needle deployment device and a proximal end of the catch; and a return spring disposed on a distal end of the catch. The needle deployment device may further include a release lever rotatably coupled to the cover portion of the needle deployment device, and the release lever may include a latch for releasably attaching to the catch. The piston may be movable in a proximal direction to compress the compression spring against the cover and body portion. The catch may be releasably attached to the lever and the needle control mechanism may be lockable in the first position within the tubular sheath. The piston may be releasable in response to actuating of the release lever such that compressive force of the compression spring may move the piston distally along the longitudinal axis to extend the needle distally of the tubular sheath to the unlocked second position. The piston may be movable in the proximal direction by the return spring compressing against the distal face of the catch in response to releasing the compression spring, such that the needle is retractable back within the tubular sheath between the first position and the second position. The needle control mechanism may further include a guide surrounding the tubular sheath. The guide may include a slot configured to receive a slide surrounding the tubular sheath, and the slide may be extendable from a distal end of a needle deployment device, wherein the slide may be movable along the longitudinal axis relative to the guide. The slide may include one or more protrusions to catch corresponding protrusions on the guide, thereby registering the slide within the guide at predetermined locations along the guide. The needle may be hollow. A guidewire may be deployable from within the hollow needle. The distal end of the tubular sheath may include a beveled edge, a chamfered edge, a fillet, or a groove. The needle may include one or more slits in an outer perimeter of the needle.

According to an exemplary embodiment of the present disclosure, a system for accessing tissue may include a puncture device comprising: a tubular sheath extending along a longitudinal axis, and the tubular sheath having a proximal end and a distal end. A needle may be disposed coaxially in the sheath. The needle may have a proximal end and a distal end and may be movable along the longitudinal axis of sheath. A needle control mechanism may be configured to lock the distal end of the needle in a first position retracted within the distal end of the sheath, and may be configured to release the needle to an unlocked second position such that the distal end of the needle is extendable beyond the distal end of the sheath. The system may further include a steerable catheter. The catheter may be configured to receive the puncture device coaxially along a working channel of the catheter and orient the device into position with respect to the tissue.

In various of the foregoing and other embodiments of the present disclosure, the needle control mechanism may be configured to release the needle to the unlocked second position to pierce the tissue (e.g., cardiovascular tissue), thereby obtaining access through the tissue. The needle control mechanism may be configured to retract the needle back within the tubular sheath after piercing the tissue. The needle may be hollow. The catheter may include direct vision imaging components.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures:

FIG. 3 illustrates an access system in accordance with an exemplary embodiment of the present disclosure;

FIG. 4 illustrates a detail view of a distal end of the access system of FIG. 3;

FIG. 5 illustrates an exemplary embodiment of a tissue puncture device in accordance with the present disclosure;

FIGS. 7A-7D illustrate an exemplary embodiment of a needle of a tissue puncture device in accordance with the present disclosure;

FIG. 11 illustrates a partial sectional view of an assembled needle deployment device of a needle control mechanism in accordance with an exemplary embodiment of the present disclosure;

FIG. 12 illustrates a perspective view of a proximal end of an access system in accordance with an exemplary embodiment of the present disclosure;

FIGS. 13A-13B illustrate a lever of a needle deployment device in accordance with an exemplary embodiment of the present disclosure;

FIG. 17 illustrates a flow chart of an exemplary embodiment of a method for using an access system and tissue puncture device in accordance with the present disclosure.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

Although the description in the present disclosure is focused on cardiovascular devices and systems, and methods for accessing cardiovascular tissue, these and other systems, devices, and methods for any application requiring tissue to be punctured are envisioned (e.g., applications for tissue puncturing devices and systems), or methods for accessing tissue, for puncturing tissue in a uniform manner, at a repeatable depth, for automatically retracting a needle to a sheathed position, etc. For example, tissue sampling for biopsies, tunneling a needle through various types of tissue, delivery of fluids after tissue puncture, delivery of tissue markers for the passage of accessory devices, or combinations thereof, may utilize the systems, devices, and methods of the present disclosure.

Figure 2:
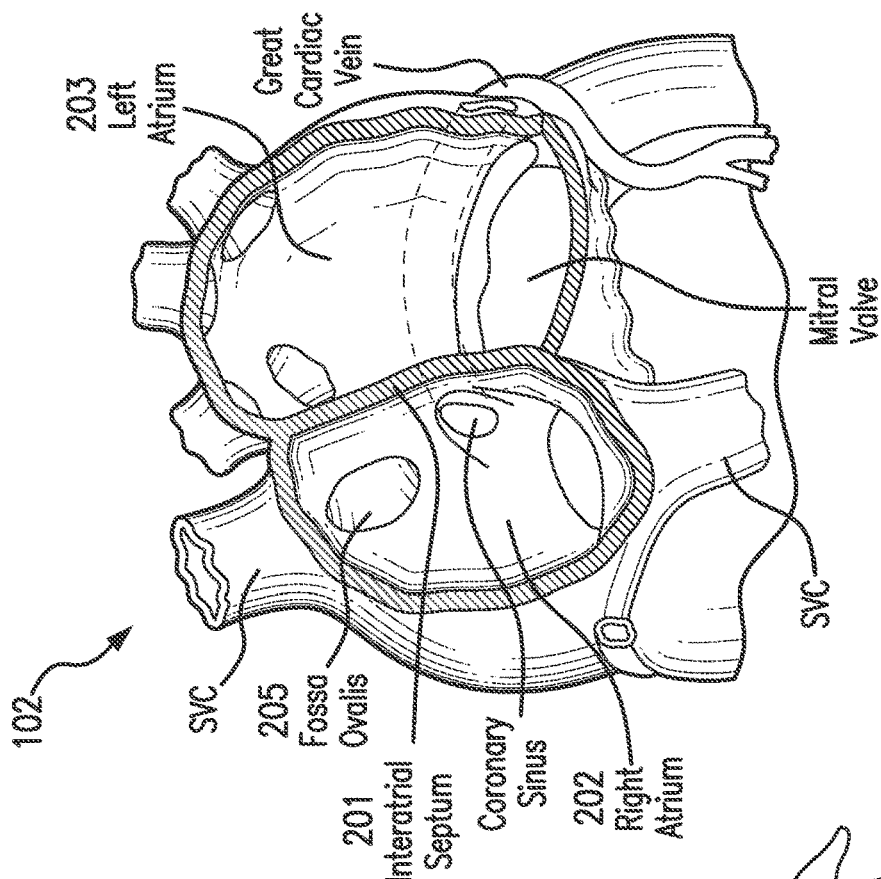
FIG. 2 illustrates a human heart.
Figure 1:
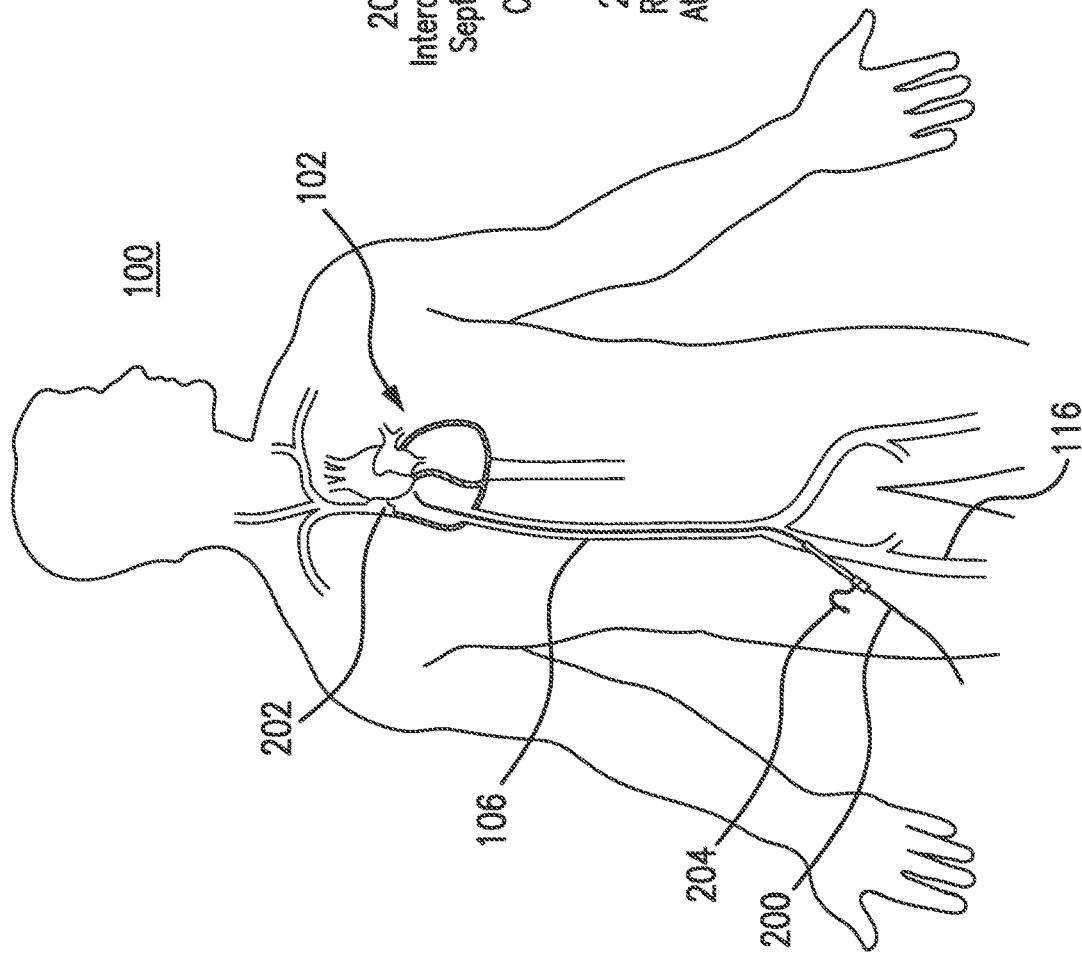
FIG. 1 illustrates access to a patient's heart by a medical device.

As described above and shown in FIGS. 1 and 2, a medical professional may perform a trans-septal procedure on a heart 102 of a patient 100 by accessing a femoral artery 116 via a catheter 204. In some embodiments, the heart 102 may be accessed via a brachiocephalic vein. The catheter 204 may be used to navigate the anatomy and guide a tissue puncture device (e.g., a cardiovascular tissue puncture device (including, e.g., a guidewire 200)) to the heart and access the heart 102 via the superior or inferior vena cava 106, so that the device may enter the right atrium 202 of the heart 102.

Access systems and puncture devices in accordance with exemplary cardiovascular embodiments of the present disclosure, may be guided to a septal wall separating the right atrium 202 and the left atrium 203 of the heart 102, and more specifically, to navigate to the fossa ovalis 205 of the septal wall. For example, systems and devices may utilize multiple navigation modalities, including but not limited to fluoroscopy, echo-cardio, direct imaging and/or lighting for location and alignment to the fossa ovalis 205. It may be advantageous for the systems and devices to align substantially perpendicular to the fossa ovalis 205 for obtaining a more direct path through the heart tissue, as well as decreasing tissue skiving and/or scraping to minimize and/or eliminate damaged tissue.

As described above, the fossa ovalis 205 is a thinner area of tissue than other areas of the septal wall, so that a needle may more easily pierce through the tissue to create a hole through the septum 201. Additionally, tissue puncture devices that may be repeatedly and reliably directed to the fossa ovalis 205 may enable a more standardized procedure across patients. Trans-septal procedures may be desirable for medical professionals to obtain access to the left atrium 203 for performing additional therapies, such as ablation and/or mitral valve repair. For example, a guidewire may be positionable at the desired location so that additional tools may be delivered over the guidewire, alone or via the catheter 204 or another introducer instrument from the femoral artery 116 and/or the brachiocephalic vein.

Access systems and puncture devices in accordance with exemplary cardiovascular embodiments of the present disclosure, may additionally be advantageous over known systems and devices by including a safety feature to selectively deploy a needle (e.g., to pierce the fossa ovalis 205) and then automatically retract a distal end of the needle within a protective tubular sheath. This may reduce risk of unintended tissue perforation (e.g., the outer heart wall tissue and/or the pericardium). This selective deployment feature of the needle may be advantageous over known systems and devices which rely on physician training, dexterity, and experience to align and pierce only the desired tissue and stop advancement of the device once the needle has deployed (e.g., crossed the fossa ovalis).

Referring now to FIGS. 3 and 4, an exemplary embodiment of an access system 300 described in the context of a cardiovascular access system in accordance with the present disclosure, is shown. A catheter 305 having a sheath 310 may be configured to extend along a longitudinal axis 301 and may be insertable in a vein of a patient (e.g., the femoral artery or the brachiocephalic vein). A tissue puncture device 340, described below, may be disposed at a proximal end of the catheter 305 and the sheath 310. It may be understood that references to "proximal" may be defined as an end of the systems and devices closest to the entry point of the patient (e.g., the femoral artery) and "distal" may be defined as an end of the systems and devices closest to the desired location of the system and devices in the patient (e.g., a patient's heart).

In some embodiments, the sheath 310 may be steerable by bending and/or flexing at least a portion of the sheath 310 to direct a distal tip 315 to the fossa ovalis 205. The sheath 310 may be articulatable by a medical professional adjusting a sheath handle 345, at a proximal end 330 of the access system 300. The catheter 305 may be steerable to translate and/or rotate axially relative to the sheath 310, and in some embodiments, may include a flexible articulation zone 320 at a distal end 325 of the catheter 305. The catheter 305 may be articulatable by a medical professional adjusting a catheter handle 350 disposed at the proximal end 330 of the access system 300. The catheter 305 may be independently steerable from the sheath 310. For example, the steerable sheath 310 may direct the catheter 305 around the inferior vena cava leading into the right atrium of the heart. The catheter 305 may then be able to articulate in order to fine tune and properly align the catheter to the fossa ovalis in the septal wall. The catheter 305 may additionally be able to articulate to view the left atrium of the heart (e.g., after the trans-septal crossing has been completed).

Figure 3A:
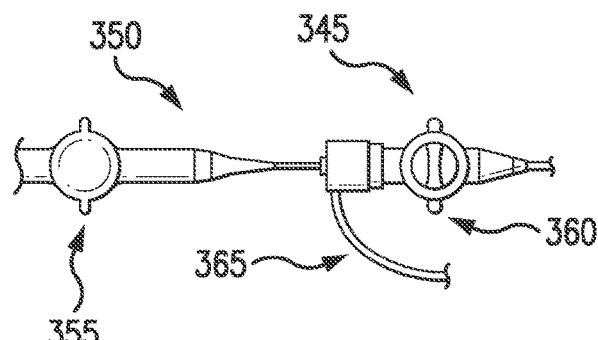
FIGS. 3A-3F illustrate embodiments of a catheter handle and a sheath handle and relative respective positions of a distal end of a sheath and catheter in accordance with the present disclosure.
Figure 3B:
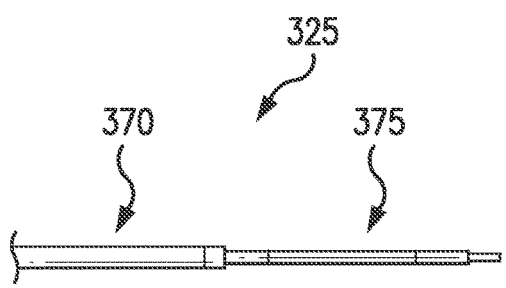
Figure 3C:
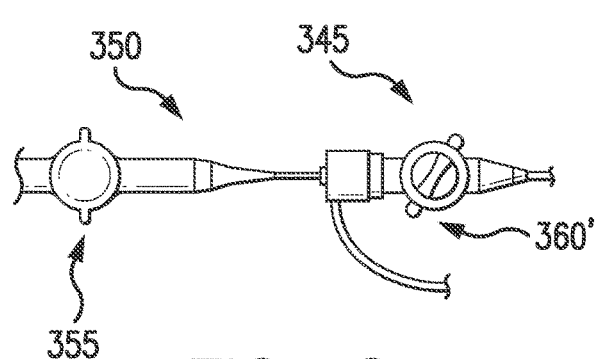
Figure 3D:
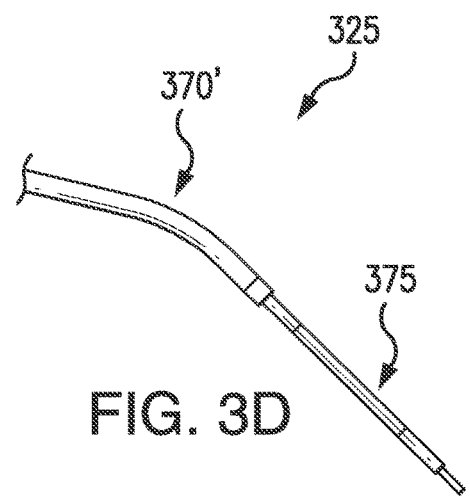
Figure 3E:
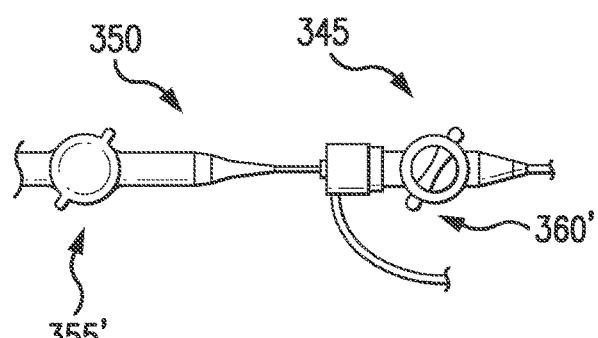
Figure 3F:
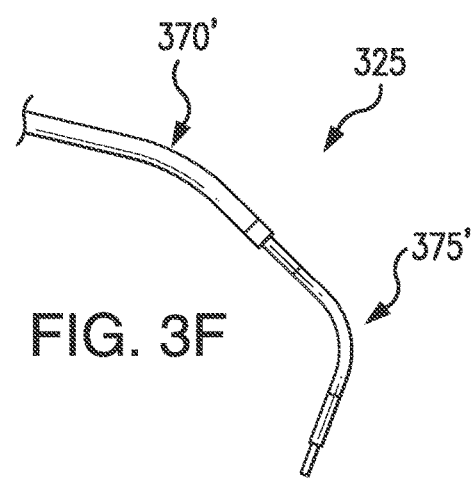
Figure 6:
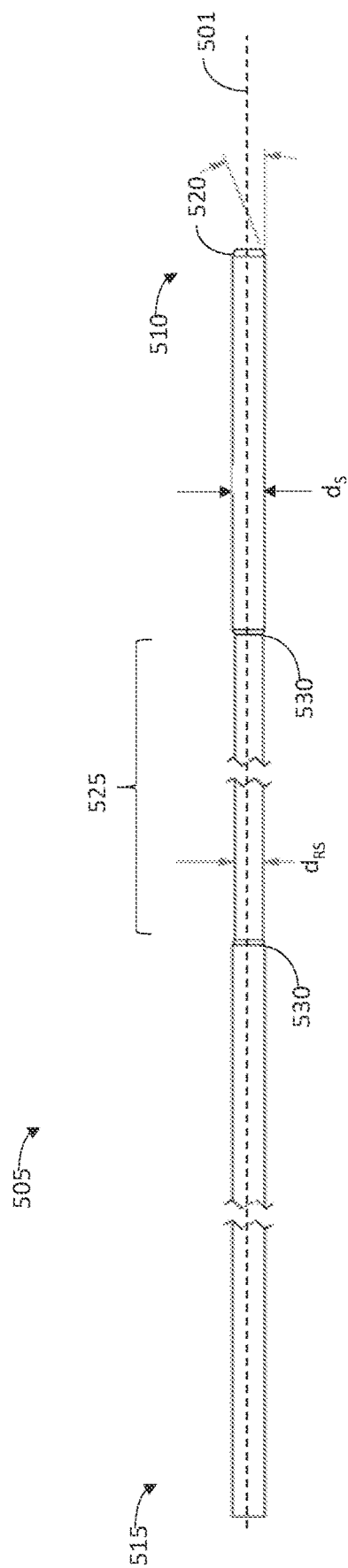
FIG. 6 illustrates an exemplary embodiment of a tubular sheath of a tissue puncture device in accordance with the present disclosure.

Referring now to FIGS. 3A-3F, embodiments of the catheter handle 350, the sheath handle 345, and the relative position of the distal end 325 of the catheter 305 and sheath 310 are shown. FIGS. 3A-3B illustrate that when the catheter handle 350 is in a straight position and the sheath handle 345 is in a straight position, the distal end 325 of the catheter 305 and the sheath 310 are each in a straight position, as shown by reference numerals 370 and 375. The catheter handle 350 may have an articulatable portion 355, and the sheath handle may have an articulatable portion 360. The distal end 325 of the catheter 305 and the sheath 310 may be in a straight position when delivering the access system 300 to the desired treatment site of the patient (e.g., the right atrium of the heart). When the medical professional desires to articulate the distal end 325 of the catheter 305 and/or the sheath 310, the articulatable portions 355, 360 of the respective catheter handle 350 and the sheath handle 345 may be adjusted. As shown in FIGS. 3C-3D, the medical professional may desire to keep the catheter 305 in a straight position 375, and articulate the sheath 310 to a bent position 370'. The articulatable portion 360 may be adjusted as shown by reference numeral 360'. As shown in FIGS. 3E-3F, when the medical professional desires to move both the distal end 325 of the catheter 305 and the sheath 310 to bended positions 375', 370', respectively, the articulatable portions 355, 360 may be both adjusted. For example, the articulatable portion 355 of the catheter handle 350 may be adjusted to a position shown by reference numeral 355', and the articulatable portion 360 of the sheath handle 345 may be adjusted to a position shown by reference numeral 360'.

The catheter 305, sheath 310, and/or the distal tip 315 may be a lumen, such that additional tools and devices, for example, a guidewire 335, may be deliverable to the targeted treatment site (e.g., the fossa ovalis 205) via the catheter 305, the sheath 310, and/or the distal tip 315. In some embodiments, the catheter 305 may include one or more working channels inside the catheter 305 for delivering one or more tools, end effectors, imaging systems, lighting systems, and the like, to the targeted treatment site. For example, in some embodiments, saline may be transported to the treatment site, which may be used to displace blood so that an imaging device may directly view the tissue for puncturing. Saline may additionally lubricate tubing surfaces for improved translation performance of the access system 300. For example, a sheath port 365 may disposed at the sheath handle 345 for additional lubricity between an inner diameter of a sheath 310, and an outer diameter of a catheter 305.

The distal tip 315 may include means for direct visualization while navigating to the desired location. For example, the distal tip 315 may include one or more imaging devices, e.g., cameras, and/or one or more lighting devices, such as light emitting diodes (LEDs) (see e.g., FIGS. 14-16). In some embodiments, fiber optics may be used to provide direct imaging and/or lighting to the distal tip 315. The distal tip 315 may further include a transparent balloon surrounding imaging devices, lighting devices, and the like. The balloon may include a concave folded region, for example, a portion of the balloon may be inverted on itself. The balloon may be filled with fluid, for example, a sterile saline, so that the balloon is expandable to displace blood away from the desired heart tissue. The imaging devices and/or the lighting devices may transmit and receive light through the balloon so a medical professional may have direct visualization of the desired heart tissue to perform a trans-septal procedure. For example, direct visualization may allow a physician to navigate the distal tip 315 to the fossa ovalis 205 and verify proper alignment to improve deployment of a tissue puncture device 340 over known devices and systems.

The access system 300 may further include a tissue puncture device 340, as described in the context of a cardiovascular tissue puncture device, illustrated by exemplary embodiments shown in FIGS. 5, 6, and 7A-7D. The tissue puncture device 340 may include a tubular sheath 505 having a distal end 510 and a proximal end 515, extendable along longitudinal axis 501. In embodiments, the longitudinal axis 501 may be coaxial and/or co-linear to the longitudinal axis 301. The tubular sheath 505 may be a hollow tube having a diameter ds (e.g., for retaining a needle) and may be configured for flexible articulation for improved positioning for the trans-septal procedure. For example, the tubular sheath 505 may include a section 525 of a reduced diameter $d_{RS}$. The section 525 may be reduced by tapers 530, including but not limited to a bevel, a chamfer, a fillet, a groove, and the like. In some embodiments when the access system 300 is assembled, the section 525 may be aligned with the flexible articulation zone 320 of the catheter 305 when the tubular sheath 505 is fully retracted within the sheath 310 of the catheter 305. In some embodiments, the tubular sheath 505 may be extendable from the distal end 325 of the catheter 305, when the catheter 305 is positioned in a right atrium of a patient's heart, prior to firing the needle. The tubular sheath 505 may be in a retracted position during positioning of the access system 300. In embodiments, the tubular sheath 505 may be formed of a metal and/or a plastic material (e.g., PEEK).

The distal end 510 of the tubular sheath 505 may further include a tapered edge 520 (e.g., a beveled edge, a chamfered edge, a fillet, and/or a groove). In embodiments, the edge 520 may have an angle between approximately 5 and 30 degrees, and may be approximately 20 degrees. A taper that is more shallow may deflect, or deform, more readily, compared to a less shallow taper, during extension through the working channel within the catheter, and thinner material may deflect, or deform, during tissue tenting, as described below. The tapered edge 520 may be advantageous over a substantially perpendicular edge (e.g., 90 degrees±10 degrees) so that distal movement through the tissue may be less tortuous and may minimize tissue damage. Additionally, tapered edge 520 may allow for the tubular sheath 505 to more easily translate (as compared to non-tapered edges) within the catheter 305 (e.g., to avoid catching on transition areas between different components). The tapered edge 520 may also allow the tubular sheath 505 to more efficiently follow the needle through the pierced tissue. The edge 520 of the tubular sheath 505 may allow the medical professional to apply forward pressure to advance the device by minimizing potential tissue damage when positioning the distal end 510 at the fossa ovalis 205. In some embodiments, tissue surrounding the tubular sheath 505 may be tented and tensile forces may be applied by the edge 520 as the distal end 510 is positioned for performing a trans-septal procedure.

A needle 705 extending along longitudinal axis 701 may be disposable within the tubular sheath 505, and may be coaxial and/or co-linear to longitudinal axis 501 of the tubular sheath 505. The needle 705 may have a distal end 710 and a proximal end 715, and may be movable within the tubular sheath 505 along the longitudinal axes 501, 701 so that the distal end 710 of the needle 705 may be selectively extendable beyond a distal end 510 of the tubular sheath 505 (see e.g., FIG. 16).

The distal end 710 of the needle 705 may include a pointed tip 720, for example, formed by one or more tapers, bevels, chamfers, fillets, and/or grooves. As shown in FIGS. 7B-7C, the distal end 710 of the needle 705 may include at least two angles 725, which may enhance the pointed tip 720, and may be advantageous for point integrity. This double-cut (e.g., a Lancet) may provide a straighter cut through tissue using less force and trauma than a single cut. The pointed tip 720 may allow for piercing of the fossa ovalis 205 when the needle 705 is selectively extended beyond a distal end 510 of the tubular sheath 505.

In some embodiments, the needle 705 may be hollow (e.g., for deploying additional tools and/or therapies). For example, a guidewire may be deployed from a hollow needle, and/or additional solutions for treating and/or imaging the desired area may be deployed (see e.g., FIG. 16).

Figure 7A:
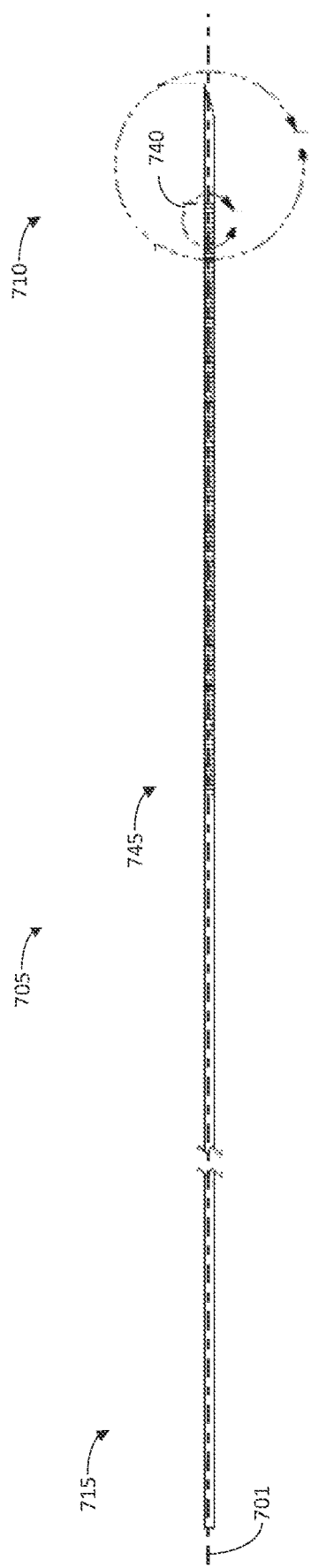

In some embodiments, the needle 705 may further include one or more slits 730, for example, circumferential grooves cut into an outer perimeter 735 of the needle 705 illustrated in FIG. 7D as a detail view 740 of FIG. 7A. In embodiments, the slits 730 may be cut through the outer perimeter 735, and may extend around the outer perimeter 735 less than 360°. The slits 730 may be disposed axially on the needle 705 along the longitudinal axis 701, and may be unconnected from each other to maintain structural integrity of the needle 705. The slits 730 may be disposed in pairs, and material between each slit pair may bend during articulation and may allow for translating forces used for piercing through tissue (e.g., compressive forces) and retracting the needle (e.g., tensile forces). The slits 730 may be positioned along the longitudinal axis 701 of the needle 705 from approximately the distal end 710 of the needle 705 to a central portion 745 of the needle 705. Including cuts, grooves, and/or slits along a length of the needle may be advantageous to provide additional flexibility as it is advanced towards a patient's heart.

The tissue puncture device 340 may further include a needle control mechanism 535, disposed at a proximal end 515 of the tubular sheath 505 and the proximal end 715 of the needle 705. In embodiments, the needle control mechanism 535 may include a guide 540 (e.g., a telescoping guide) and a cover 545, and in some embodiments, may be a handle for the medical professional to articulate the access system to perform the trans-septal procedure (see e.g., FIGS. 5, 8A-8B, and 9). In embodiments, the guide 540 may extend along the longitudinal axis 501, and may be substantially cylindrical. The needle control mechanism 535 may further include a needle deployment device 550 disposed at a proximal end of the needle control mechanism 535. In some embodiments, the guide 540 may include a slot 555 for receiving at least a portion of the needle deployment device 550. The slot 555 may extend along the longitudinal axis 501, and may have a size and/or a shape configured to mate with at least a portion of the needle deployment device 550 (e.g., a slide 815). The slide 815 may be movable along the longitudinal axis 701 relative to the guide 540, for example, in a telescoping motion. In embodiments, the guide 540 and the slide 815 may move both the tubular sheath 505 and the needle 705 relative to the catheter 305. For example, a proximal end of the tubular sheath 505 may be fixedly attached to the distal end of the slide 815 (e.g., at reference numeral 840). The tubular sheath 505 and the slide 815 may be attached in various manners, including but not limited to mechanical fasteners, adhesive, bonding, and the like.

Figure 8A:
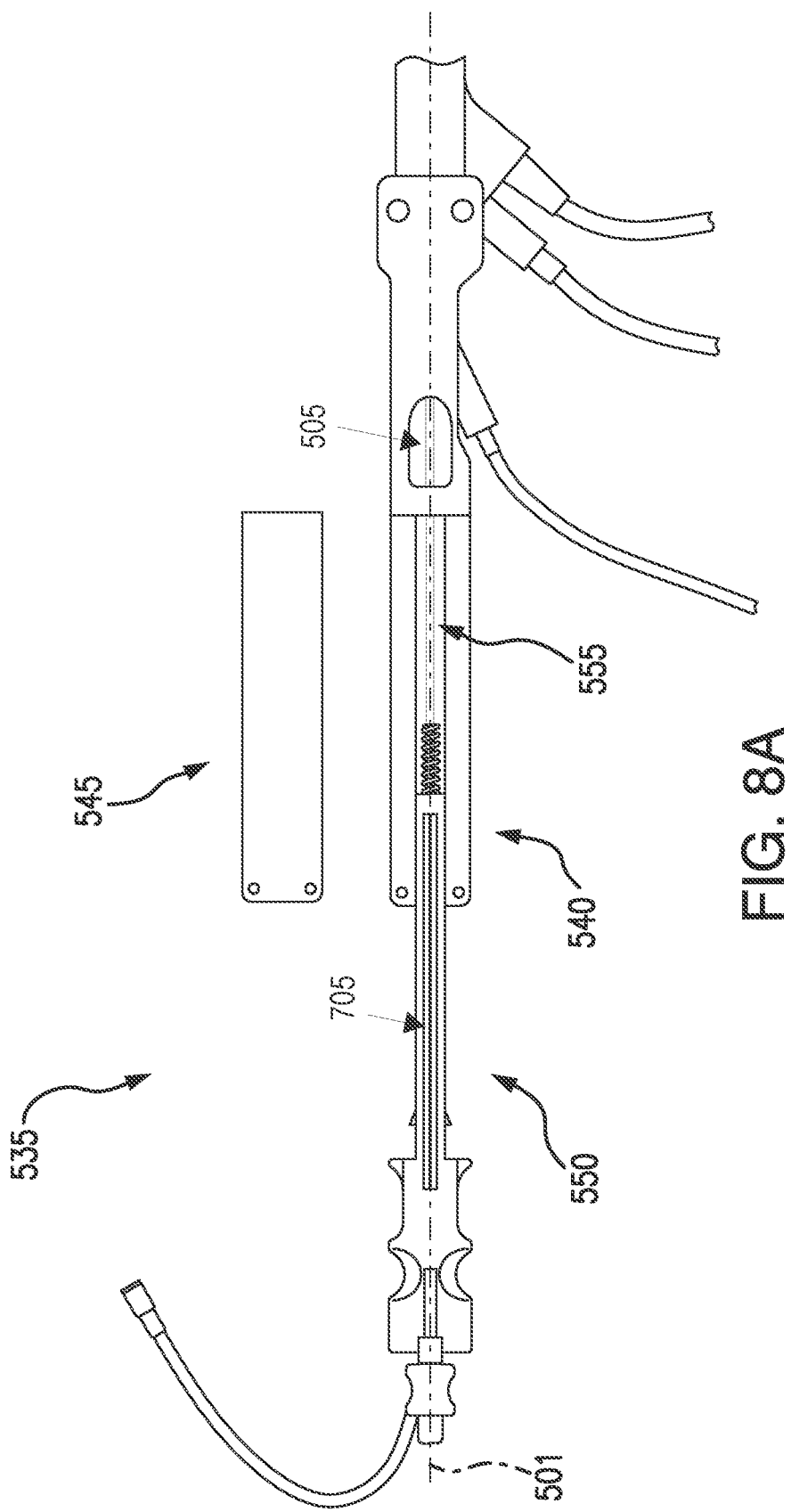
FIGS. 8A-8B illustrate a needle control mechanism of a tissue puncture device in accordance with an exemplary embodiment of the present disclosure.
Figure 8B:
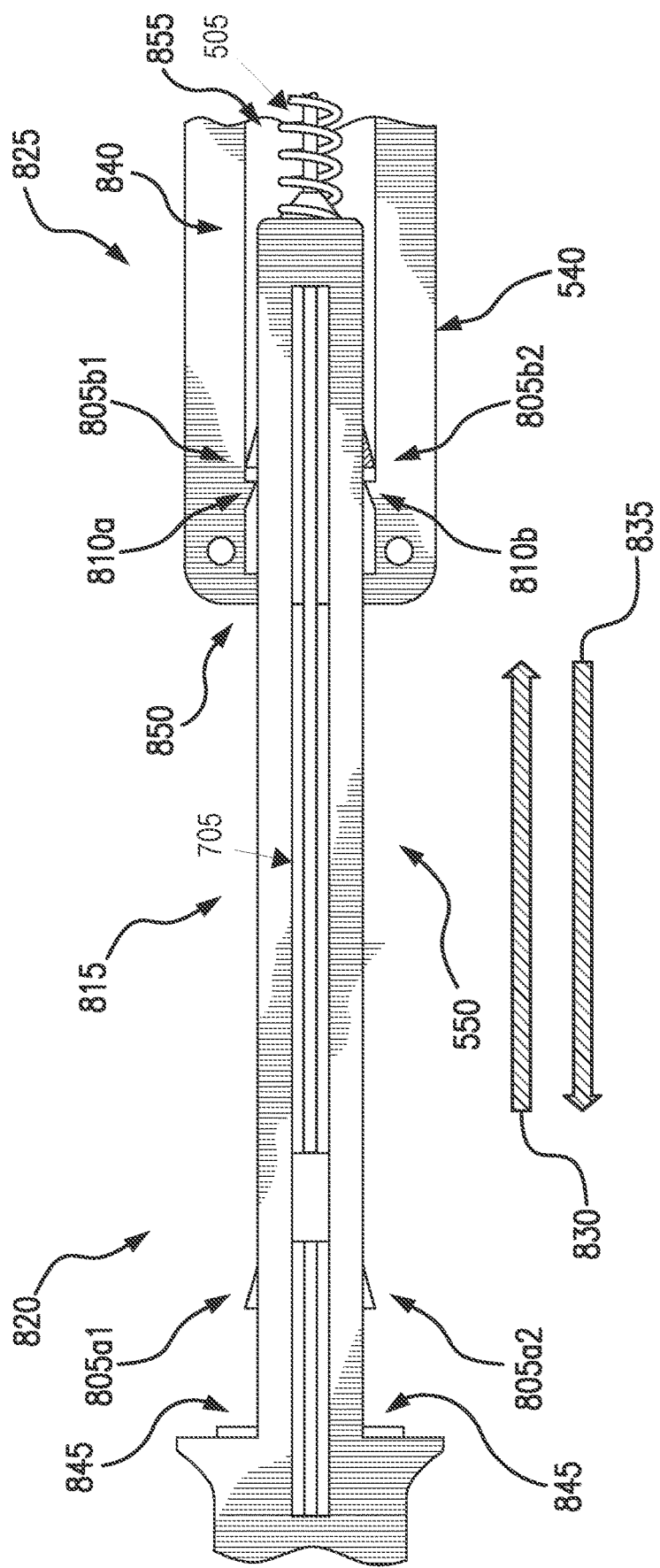

Referring to FIGS. 8A-8B, the slide 815 may include protrusions 805a1, b1, . . . n, extending radially from the slide 815. The protrusions may be formed in pairs (e.g., 805a1, 805a2, and 805b1, 805b2) where the protrusions of the respective pairs may be formed parallel to each other on opposite sides of the slide 815. For example, the protrusion 805a1 may be opposite the protrusion 805a2 on the slide 815. Additionally, each pair of protrusions may be formed along a length of the slide, so that protrusions 805a1, 805a2 may be at a proximal end 820 of the slide 815 and the protrusions 805b1, 805b2 may be a distal end 825 of the slide 815. In some embodiments, the protrusions 805a1, 805a2, and 805b1, 805b2 may be formed as barbs.

In some embodiments, the guide 540 may include one or more protrusions 810a, 810b, extending into the slot 555. The protrusions 810a, 810b may be pairs (e.g., formed on opposite sides of the slot 555) so that the protrusions 810a, 810b are substantially parallel to each other. In embodiments, the protrusions 810a, 810b may be formed as barbs to prevent proximal movement of the slide 815. For example, as the slide 815 is moved in a distal direction (e.g., in a direction indicated by arrow 830), protrusions 805b1, 805b2 may pass protrusions 810a, 810b of the guide 540. If the slide 815 were to be then moved in a proximal direction (e.g., in a direction indicated by arrow 835), the protrusion 810a would abut against the protrusion 805b1, and the protrusion 810b would abut against the protrusion 805b2, so that the slide 815 is stopped from telescoping out of the guide 540. Additionally, as the slide 815 is moved in a more distal direction, the protrusions 805a1, 805a2 may similarly pass the protrusions 810a, 810b of the guide 540, and abut against each other in response to moving the slide in a proximal direction. In some embodiments, a spring 855 may be disposed at the distal end of the slide 815, for maintaining a constant pressure between the protrusions 810a, 810b, and protrusions 805a1, 805a2, 805b1, 805b2. The spring 855 may be a helical spring, with the tubular sheath 505 extending coaxially in a longitudinal direction (e.g., along longitudinal axis 501, 701).

When the slide 815 is at a first position (e.g., protrusions 805b1, 805b2) are engaged with protrusions 810a, 810b, the needle 705 and the tubular sheath 505 may be in a retracted position. This first position may allow the catheter 305 to articulate (e.g., as the access system 300 is being positioned in the patient to the right atrium). When the slide 815 is at a second position (e.g., protrusions 805a1, 805a2 are engaged with protrusions 810a, 810b) the distal end 510 of the tubular sheath 505 may be aligned with the distal end 325, which may allow saline to flow between the tubular sheath 505 and the working channel of the catheter 305, as described below. The needle 705 may be prepared to be fired once the slide 815 is at the second position.

When the slide 815 is at a third position (e.g., when surface 845 contacts surface 850) the tubular sheath 505 may be extended from the distal end 325 (e.g., see FIG. 15), and the needle 705 may be advanced to extend out of the tubular sheath 505. For example, a distal face of a body portion, described below, may contact a proximal face of the guide 540. At this third position, the tubular sheath 505 may be extended into a patient's tissue (e.g., when at the desired position of the treatment site) thereby resulting in a "tenting" action through application of tensile forces on the tissue. This tenting action may allow the tissue (e.g., of the septal wall, to be more easily cut).

Figure 9:
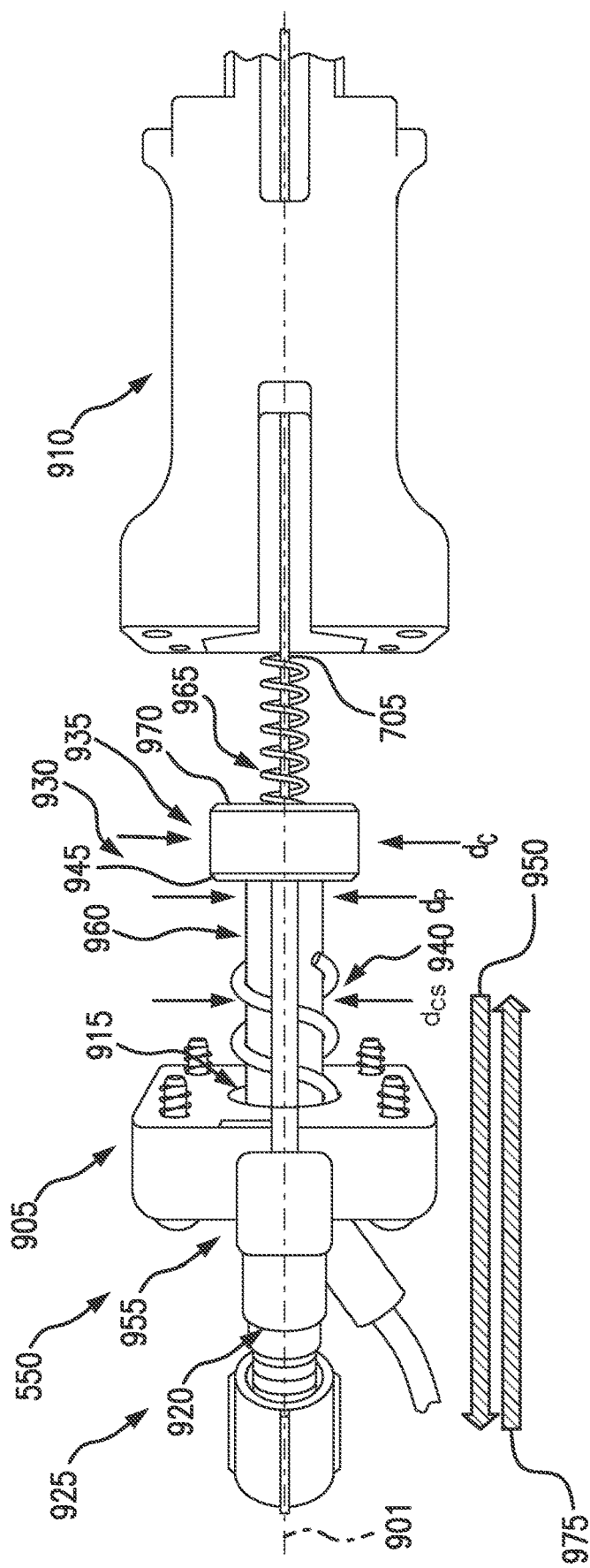
FIG. 9 illustrates an exploded view of a needle deployment device of a needle control mechanism in accordance with an exemplary embodiment of the present disclosure.
Figure 10:
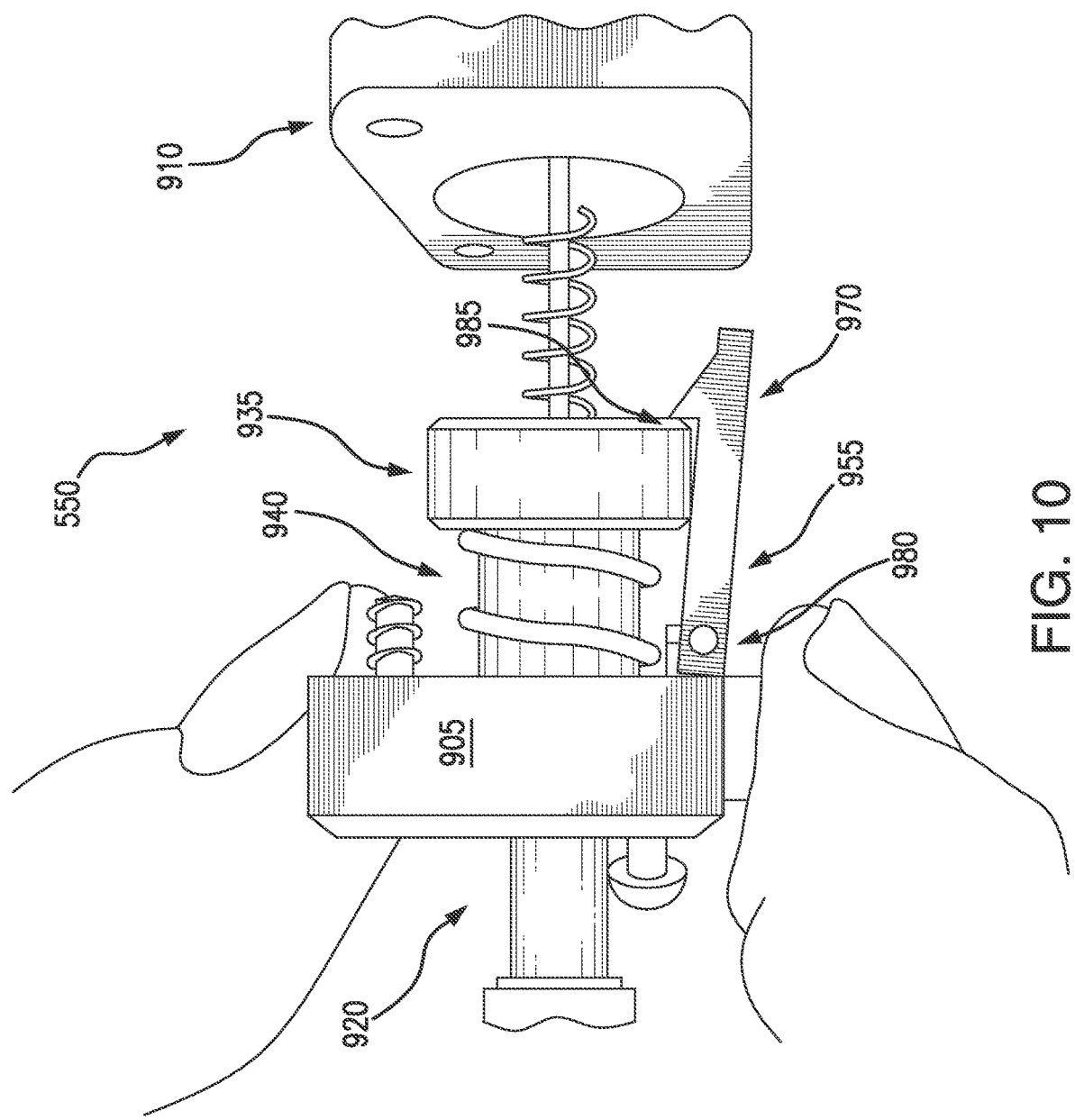
FIG. 10 illustrates an exploded view of a needle deployment device of a needle control mechanism in a locked position in accordance with an exemplary embodiment of the present disclosure.

Referring now to FIGS. 9-12, an exemplary embodiment of a proximal end of the needle deployment device 550 in accordance with the present disclosure is shown. FIGS. 9 and 10 illustrate a needle deployment device 550 in an exploded, or disassembled state. FIG. 11 illustrates the needle deployment device 550 in an assembled state. A cover portion 905 may be couplable to a body portion 910 (e.g., by one or more mechanical fasteners, hinges, screws, bolts, clips, rivets, solder, welding, adhesive, and the like). Although the cover portion 905 and the body portion 910 are shown as separate elements, it is understood that the cover and the body may be integrally formed in some embodiments. The cover portion 905 may include an aperture 915, for receiving a piston 920. The piston 920 may extend along a longitudinal axis 901, and may be sized and shaped to fit through the aperture 915. In some embodiments, the aperture 915 may be a substantially circular through-hole for receiving a substantially cylindrical piston 920, although any shape for deploying a needle is envisioned.

The piston 920 may be movable relative to the cover portion 905 and the body portion 910 along the longitudinal axis 901. When the needle deployment device 550 is assembled, a proximal end 925 of the piston 920 may extend out of the cover portion 905 in a proximal direction, and a distal end 930 of the piston 920 may be disposed internal to the body portion 910 and/or the cover portion 905. In some embodiments, the distal end 930 of the piston 920 may be couplable to the proximal end 715 of the needle 705, so that the needle 705 is movable along the longitudinal axis 701, 901 in response to the medical profession translating the piston 920. A catch 935 may be coupled to the distal end 930 of the piston 920, and may also be connected to the proximal end 715 of the needle 705 (e.g., by mechanical fasteners, adhesive, press fit, weld, solder, and the like). In some embodiments, the catch may be a disc, a block, or any configuration having a diameter $d_C$ greater than a diameter $d_P$ of the piston 920. The catch 935 may be formed of an inflexible material, (e.g., such as a metal, including but not limited to a medical grade stainless steel).

A compression spring 940 may be extendable along the distal end 930 of the piston 920 and the longitudinal axis 901, and may have a diameter $d_{CS}$ larger than the diameter $d_C$ of the piston 920. The compression spring 940 may be a helical spring, and compressible between the catch 935 and the cover portion 905. The diameter $d_C$ of the catch 935 may be greater than the diameter $d_P$ of the piston 920 and of the diameter $d_{CS}$ of the spring so that the compression spring 940 abuts against a proximal face 945 of the catch 935. For example, when the piston is moved in a proximal direction (indicated by arrow 950), the catch 935 compresses the compression spring 940. For example, the compression spring 940 may abut against the cover portion 905. In some embodiments, the compression spring 940 may be disposed in a recessed area of the cover portion 905 (see FIG. 11). The compression spring 940 may apply a force against the cover portion 905 and the catch 935, as a medical professional moves the piston 920 in a proximal direction (e.g., loading the compression spring 940 with stored energy).

The needle deployment device 550 may further include a release lever 955, which may be rotatably coupled to the cover portion 905 (see FIG. 10). In some embodiments, the release lever 955 may be pivotably coupled to the cover portion 905, for rotational movement of the release lever 955 about a pin 980. The lever 955 may include a latch 960 configured to releasably attach to the catch 935. For example, when the piston 920 is moved in the proximal direction 950 to compress the compression spring 940, the latch 960 may attach to the catch 935, to hold the piston and the compression spring 940 in a retracted position (see FIG. 10).

The needle deployment device 550 may further include a return spring 965, extending distally of the distal end 930 of the piston 920 and/or a distal face 970 of the catch 935. In embodiments, the return spring 965 may have a spring constant different than a spring constant of the compression spring 940, so that the piston 920 may be movable by compressive forces of the compression spring 940 and the return spring 965. The spring constant of the compression spring 940 may be selected so that the compressive force of the compression spring 940 may be of a force sufficient to move the piston 920 and the needle 705 in a distal direction to pierce through the fossa ovalis. The spring constant of the return spring 965 may be selected so that the compressive force of the return spring 965 may be of a force sufficient to move the piston 920 and the needle 705 in a proximal direction to reverse the movement caused by the compressive force of the compression spring 940. In embodiments, the return spring 965 and/or the compression spring 940 may be formed of a medical grade stainless steel.

Referring now to FIG. 10, the piston 920 and the catch 935 are shown in a retracted position (e.g., the latch 960 is attached to the catch 935 so that the compression spring 940 is held in a compressed state between the cover portion 905 and the catch 935). This compressed state may hold the needle 705 in a retracted locked position (e.g., so that the distal end 710 of the needle 705 is not extended beyond a distal end 510 of the tubular sheath 505).

As described above, the latch 960 may hold the compression spring 940 in a compressed state, so that the piston 920 is in a retracted position. When the access system is positioned in a patient and at the appropriate area of the heart (e.g., positioned substantially perpendicular at the septal wall) the medical professional may actuate the release lever 955 to release the latch 960 from the catch 935. In some embodiments, the release lever 955 may be pivotably rotated to release the latch 960 from the catch 935. In embodiments, the lever 955 may have a hinge, or pin 980 to rotatably couple the lever 955 to the cover portion 905.

The return spring 965 may be a helical spring, extending along the longitudinal axis 901, and configured so that the needle 705 extends within the helical spring. The return spring 965 may be compressible when the latch 960 releases the catch 935 (e.g., when compressive forces of compression spring 940 move the piston 920 and the catch 935 in a distal direction 975). This release movement may result in a needle 705 extending beyond a distal end 510 of a tubular sheath 505 (e.g., "firing" the needle to pierce desired tissue). The return spring 965 may abut against an internal edge of the body portion 910 and the distal face of the catch to compress and thereby move the piston 920 and the catch 935 in the proximal direction 950. This retraction movement may result in a needle 705 retracting back within the tubular sheath 505 between the extended, unlocked ("fired") position and the retracted, locked ("for firing") position.

This automatic retraction motion by the return spring 965 may be advantageous over known systems and devices to mitigate unintended tissue damage. For example, a medical professional using existing systems and devices would need to manually extend the needle to pierce through the septal wall, as well as to retract the needle after piercing the tissue, relying only on experience of touch, distance, and manual dexterity to use appropriate force for piercing tissue and to not over extend the needle. The present disclosure reduces potential for error by automatically moving the needle in a proximal direction after a predetermined distance (e.g., approximately 3 to 10 mm). In this manner, the fossa ovalis may be pierced with sufficient force by the compressive force of the compression spring 940, and retracted by the return spring 965 before extending beyond the desired location. This may mitigate unintended tissue and/or vein damage of the heart (e.g., outer heart wall tissue and the pericardium).

Referring now to FIG. 11, the needle deployment device 550 may include a cover portion 905 and a body portion 910, the body portion 910 having an aperture 915 for receiving at least a portion of the piston 920, the compression spring 940, the catch 935, and the return spring 965. The compression spring 940 may abut a recessed portion 1105 of the cover portion 905. The cover portion 910 may extend along the longitudinal axis 1101, and may allow a needle 705 to extend from the piston 920 to the distal end of the access system. In some embodiments, a tubular sheath 505 may be attached to the body portion 910, and extendable along the longitudinal axes 501, 701, 901, 1101. In embodiments, the longitudinal axes 501, 701, 901, 1101, may be coaxial and/or co-linear. The body portion 910 may also include a slot 1110, extending along the longitudinal axis 1101, the slot 1110 being configured to receive at least a portion of the release lever 955. For example, the lever 955 may slide into the slot 1110 so the body portion 910 may not interfere with the attachment of the lever 955 to the cover portion 905 and the catch 935 (see FIG. 11).

As described above, the slide 815 may extend from the body portion 910, and in some embodiments may be integrally formed. In some embodiments, the body portion 910 may include one or more stops, configured to abut the guide 540, when the body portion 910 and the slide 815 are moved in a distal direction relative to the guide 540.

Referring now to FIGS. 13A-13B, an exemplary embodiment of a release lever 955 in accordance with the present disclosure is shown. The lever 955 may have an arm 1305 having a first end 1310 and a second end 1315. A pad 1320 may be disposed at the first end 1310 of the arm 1305, and a latch 1325 may be disposed at the second end 1315 of the arm 1305. In embodiments, the latch 1325 may be the latch 960 illustrated in FIGS. 9-11. The arm 1305 may further include an aperture 1330 (e.g., a through hole) for attaching the lever 955 to the cover portion 905 of the needle deployment device 550. In embodiments, the lever 955 may be rotatably coupled to the cover portion 905, so that a pin, or hinge, may allow the lever 955 to rotate about axis 1335 in a direction indicated by arrow 1340. In some embodiments, the lever 955 may be pivotable about the axis 1335. For example, the pad 1320 may be disposed on and/or extend from an upper surface 1345 of the arm 1305, and the latch 1325 may be disposed on and/or extend from a lower surface 1350 of the arm 1305. A medical professional may depress pad 1320, resulting in rotation of the lever 955 about axis 1335, thereby raising the latch 1325. As described above, the latch 1325 may release the catch 935 so that the piston 920 may move the needle 705 in a distal direction.

In embodiments, when assembled in the needle deployment device 550, the arm 1305 may extend coaxially to the longitudinal axis 901, with the pad 1320 arranged towards the proximal end 925 of the needle deployment device 550, and the latch 1325 disposed towards the distal end 930 of the needle deployment device 550. The aperture 1330 may be disposed towards the pad 1320 (e.g., towards the proximal end of the arm 1305). In some embodiments, the pad 1320 may have a flat portion 1355 so that the medical professional may easily deploy the needle 705 when desired, however, the pad 1320 may be any configuration that allows rotation of the lever 955.

The latch 1325 may be a protrusion (e.g., having an angled face 1360 and a straight face 1365). For example, the latch 1325 may be a wedge shape, so that when the piston 920 is moved in a proximal direction to compress the compression spring 940, the catch 935 may slide along the angled face 1360 until the distal face 970 mates with the straight face 1365 to retain the catch 935 (e.g., shown at reference numeral 985). As described above, the lever 955 may retain the catch 935, thereby holding the piston 920 and thus the needle 705 in a retracted position.

Figure 14:
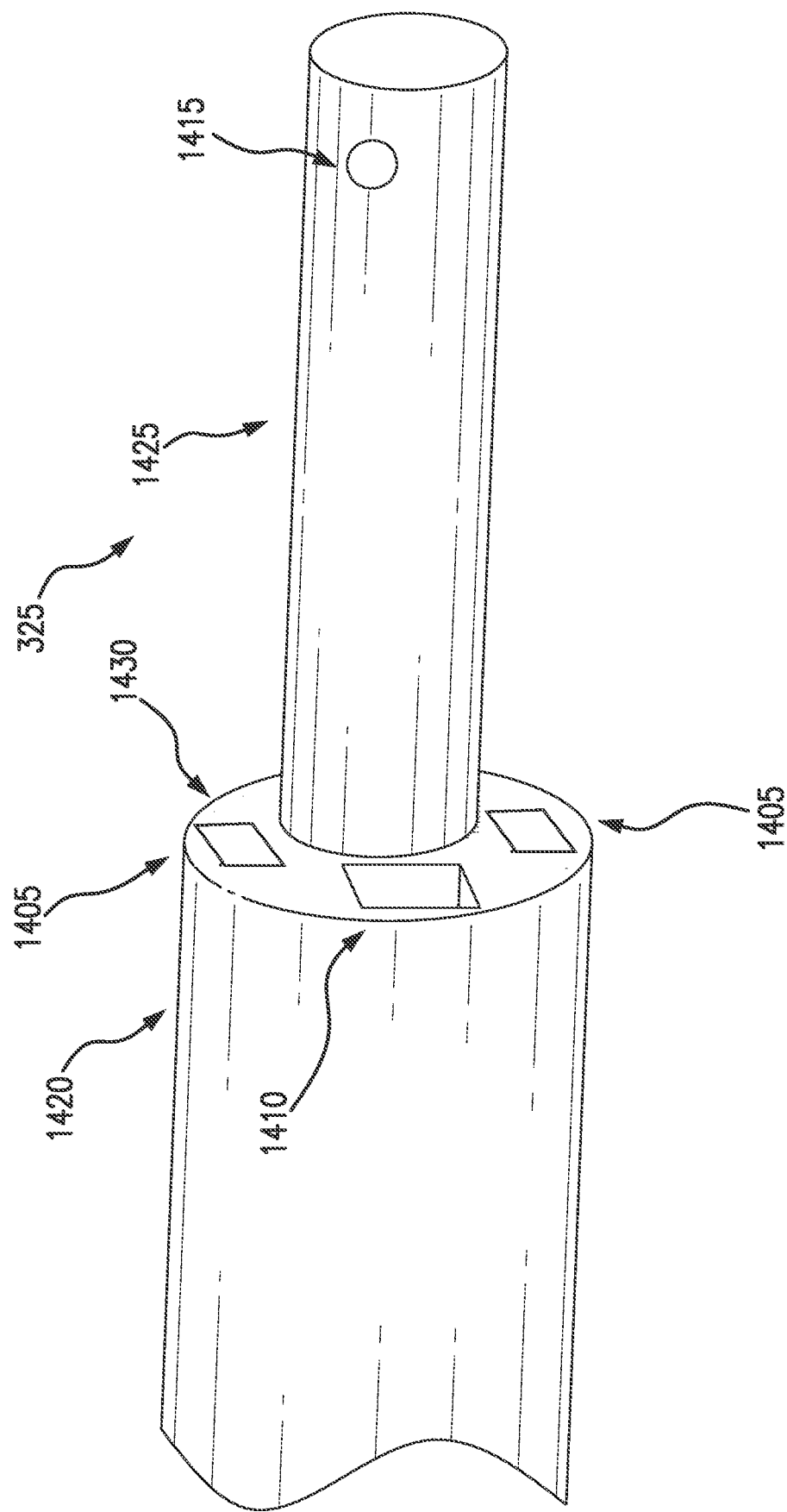
FIG. 14 illustrates a distal end of an access system and a tissue puncture device in a retracted position in accordance with an exemplary embodiment of the present disclosure.
Figure 15:
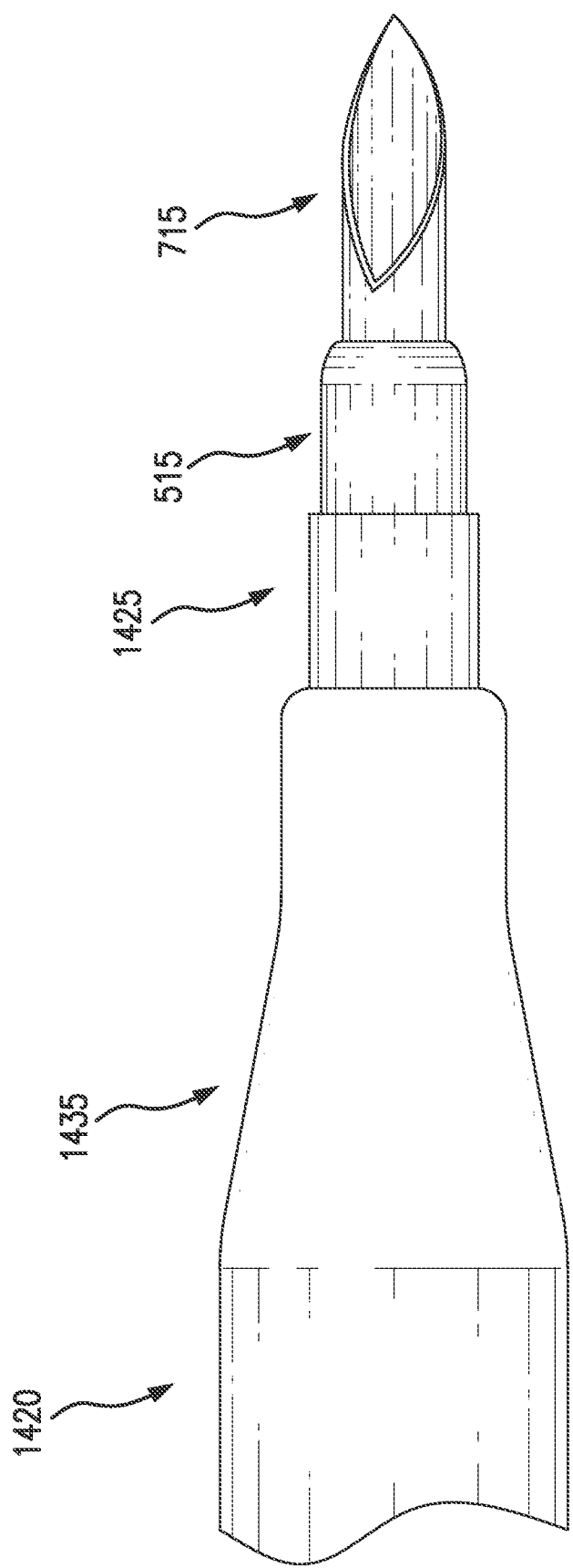
FIG. 15 illustrates a distal end of an access system and a tissue puncture device in an extended position in accordance with an exemplary embodiment of the present disclosure.
Figure 15A:
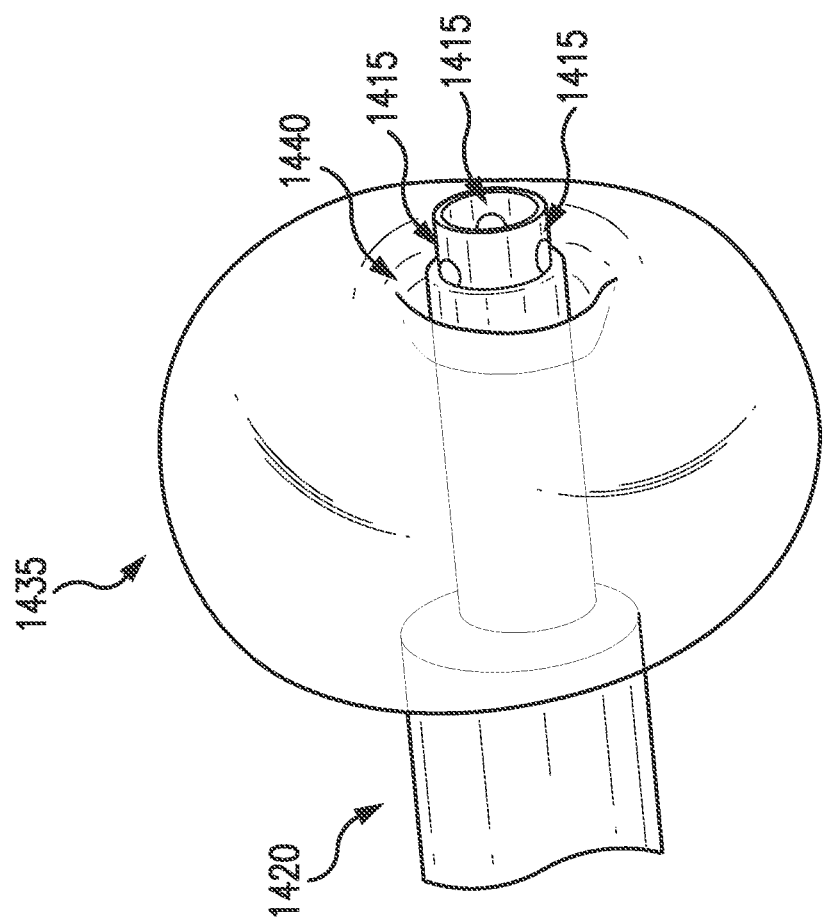
FIG. 15A illustrates a distal end of an access system and tissue puncture device having an inflated balloon in accordance with an exemplary embodiment of the present disclosure.
Figure 16:
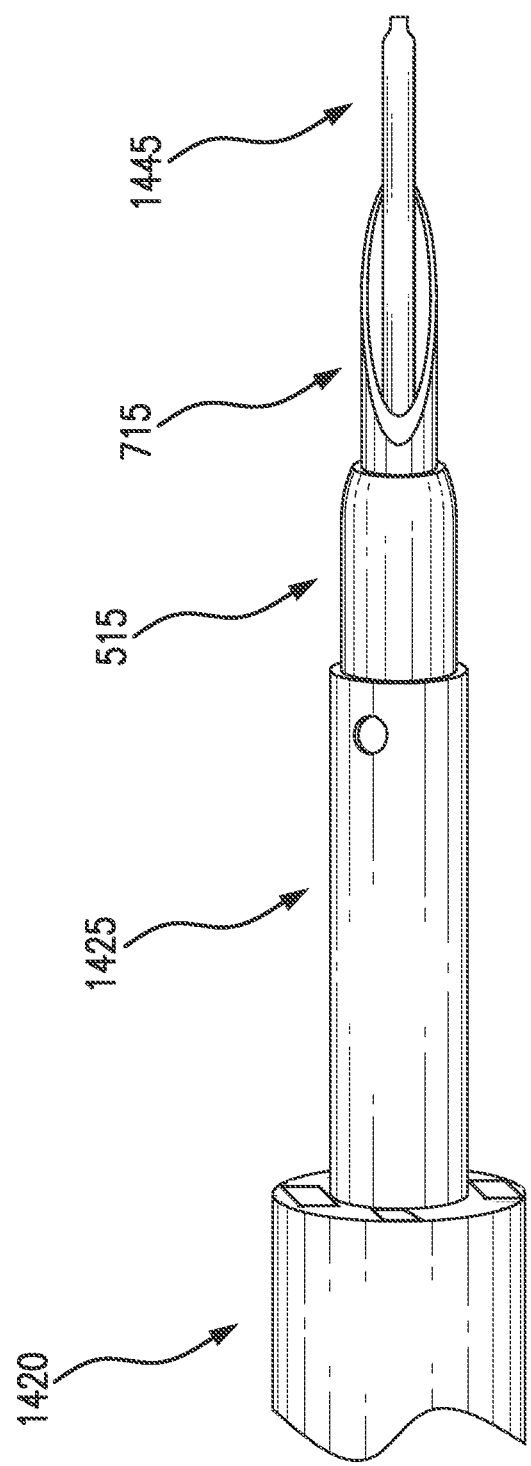
FIG. 16 illustrates a distal end of a tissue access system and a tissue puncture device in an extended position in accordance with an exemplary embodiment of the present disclosure.

As shown in FIGS. 14, 15, and 15A, the distal end 325 of the access system 300 may retain the tubular sheath 505 and the needle 705. FIG. 16 illustrates the tubular sheath 505 extending out of the distal end 325. The tubular sheath 505 may be extendable into tissue prior, during, and/or after the needle 705 is fired. The distal end 325 may include a first portion 1420 and a second portion 1425, with the first portion 1420 having a distal face 1430. As described above, the distal end 325 may include one or more lighting devices 1405, and one or more imaging devices 1410, and in some embodiments may be disposed on the distal face 1430. FIGS. 14 and 16 are shown without the balloon 1435 to illustrate the lighting devices 1405 and the imaging devices 1410. The lighting devices 1405 and the imaging devices 1410 may be advantageous to provide direct visualization for aligning the access system 300 to the desired location and position.

In some embodiments, a balloon 1435 may extend between the first portion 1420 and the second portion 1425 of the distal end 325, and may cover the lighting devices 1405 and/or the imaging devices 1410. The balloon 1435 may be transparent, and fillable with a liquid solution (e.g., saline) to provide a field of vision for the lighting devices 1405 and the imaging devices 1410. As mentioned, the balloon 1435 may have a concave folded region 1440 at its distal end, shown in FIG. 15A. The region 1440 may entrap blood that impedes a view of the targeted tissue by the imaging device. In some embodiments, the second portion 1425 may include one or more irrigation orifices 1415 (e.g., three saline flush ports). The irrigation orifices 1415 may displace the entrapped blood in the concave region to improve the view of the targeted tissue by the imaging device. Saline may flow between the distal end 325 and the tubular sheath 505 and/or the needle 705 (e.g., an inner surface of the tubular sheath and an outer surface of the needle) and out of the irrigation orifices 1415 to further clear blood and tissue from the desired field of vision. For example, the needle 705 may be a hollow tube so that saline and/or contrast may flow through, which may aid the medical professional for verifying position during fluoroscopy. This may allow the medical professional to directly visualize and confirm proper alignment of the access system prior to deploying the needle. As shown in FIG. 12, the access system 300 may further include one or more ports for delivering saline, contrast, and/or other fluids to the desired treatment site. A first port 1205 may allow for a medical professional to delivery fluid to the balloon 1435 (e.g., to fill and/or flush the treatment site). This may allow the medical professional to have a clearer view with the imaging system. A second port 1210 may be a working channel and/or a needle sheath port for saline or other fluid to be delivered to the concave folded region 1440 of the balloon 1435. This may help to clear out any entrapped blood to provide a clearer view to the medical professional. A third port 1215 may be a needle flush (e.g., for delivering contrast for fluoroscopy). In some embodiments, fluoroscopy may be used by a medical professional when confirming a position of the needle 705.

The needle 705 may be selectively extendable by the medical professional by releasing the lever 955. For example, when the access system is positioned as desired (e.g., the distal end is positioned perpendicular at the septal wall in the patient's heart), the medical professional may press the pad 1320 of the release lever 955, so that the straight face 1365 no longer contacts the catch 935. As described above, the compressive force of the compression spring 940 moves the piston 920 and the catch 935 in a distal direction, thereby "firing" the needle 705. The needle 705 may extend beyond the distal end 515 of the tubular sheath 505 to pierce tissue of the fossa ovalis and create an access hole. As further described above, once the needle is "fired," the return spring 965 may retract the distal end 715 back within the tubular sheath 505.

As described above, in some embodiments the needle 705 may be hollow so that when the needle 705 is "fired", a guidewire 1445 may be extendable out the distal end 715 of the needle 705. This may be advantageous to maintain a path through the pierced tissue, so that additional tools and/or therapies may be passed through the right atrium by accessing the left atrium of the heart by the access system. In this manner, the medical professional may then be able to perform electroporation procedures and/or valve repairs in the left atrium.

Referring now to FIG. 17, a flow chart 1700 of an exemplary embodiment of a method for using tissue access systems and puncture devices (e.g., cardiovascular tissue access systems and puncture devices) in accordance with the present disclosure, is described. Although the method steps are described in a particular order, it is understood that the steps may be performed in a different order. At step 1705, a catheter may be inserted into a patient and advanced toward the patient's heart. The catheter may be inserted via a femoral artery or a brachiocephalic vein. A distal tip of the catheter may include means for directly determining and monitoring the advancement of the catheter (e.g., imaging devices, lighting devices, fiber optics, saline balloons, etc.). At step 1710, the distal tip of the catheter may be positioned in the right atrium of the patient's heart at the septal wall, for example, so that the needle is in a first position as described above with respect to FIG. 8B. At step 1715, a slide of the needle deployment device may be disposed within and movable relative to a guide, for positioning the needle relative to the tubular sheath (e.g., in a second position as described above with respect to FIG. 8B). In some embodiments, the slide may be movable in a distal direction, and may be prevented from moving in a proximal direction by one or more protrusions (e.g., stops) on the slide and/or the guide.

At step 1720, a needle deployment mechanism may set a needle in a retracted position (e.g., by pulling a piston coupled to the needle in a proximal direction). This may compress a compression spring against a catch, and the catch may be locked by a latch of a lever. This may hold the needle in a retracted locked position until a medical profession desires to selectively extend the needle. At step 1725, a tubular sheath may be extended out of the distal tip of the catheter. The tubular sheath may have a beveled distal edge to aide in tenting tissue during positioning in the right atrium of the heart, which may mitigate tissue and vein damage.

At step 1730, the distal tip of the catheter and/or the tubular sheath may be aligned at the fossa ovalis of the septal wall so that the distal tip is substantially perpendicular to the fossa ovalis. The medical professional may be able to directly visualize the alignment of the access systems and devices to the fossa ovalis. For example, a balloon filled with saline or other fluid may help to provide a field of vision that is clear of blood and tissue for imaging devices and/or lighting devices, so that the medical professional has direct visualization of the area. The medical professional may be able to verify that the distal tip of the catheter is aligned perpendicularly to the fossa ovalis of the septal wall, and reposition the tip as needed. When the distal tip is in the desired location, the medical professional may apply forward pressure to tent the tissue with the needle sheath. Once the systems and devices are aligned properly, the medical professional may proceed with the procedure at step 1735. The lever may be manipulated by the medical professional to release the latch from the catch, so that compressive force of the compression spring extends the piston and the catch with the needle in the distal direction, to deploy or "fire" the needle to extend distally beyond the tubular sheath in an unlocked second position.

At step 1740, the needle may be automatically retracted back within the tubular sheath. A return spring may be compressed when the piston and needle extend in a distal direction during the "firing" movement. A compressive force of the return spring may result in reversing direction of movement of the needle so that the needle and/or the piston moves in a proximal direction to return the needle back within the tubular sheath between the first position and the second position.

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the subject matter of the claims.

What is claimed is:

1. An internal body tissue puncture device, the device comprising:
   a tubular sheath extending along a longitudinal axis, the tubular sheath having a proximal end and a distal end and comprising a hollow tube configured for flexible articulation within a body;
   a flexible needle disposed coaxially in the tubular sheath and advanceable within the body to puncture tissue within the body, the needle having a proximal end and a distal end and being movable along the longitudinal axis of the tubular sheath;
   a needle control mechanism configured to hold the distal end of the needle in a first position retracted within the distal end of the tubular sheath to compress a biasing element, and an unlocked second position such that expansion of the biasing element-extends the distal end of the needle beyond the distal end of the tubular sheath;
   a piston having a catch and movable along the longitudinal axis of the tubular sheath; and
   a release lever including a latch for releasably engaging the piston catch;
   wherein:
   the distal end of the piston is coupled to the needle;
   the piston is movable in a proximal direction to compress the biasing element; and
   the piston catch is releasably held by the release lever to lock the needle control mechanism in the first position.

2. The device according to claim 1, wherein the needle control mechanism includes a needle deployment device disposed at a proximal end of the needle control mechanism, the needle deployment device having a body portion couplable to a cover portion.

3. The device according to claim 2, wherein the needle deployment device includes the piston, the piston being disposed within an aperture of the cover portion such that a proximal end of the piston is external to the cover portion and the body portion and a distal end of the piston is internal to the cover portion and the body portion, wherein the piston is movable relative to the cover portion along the longitudinal axis of the tubular sheath.

4. The device according to claim 3, wherein:
   the catch is coupled to the distal end of the piston;
   the biasing element comprises a compression spring extending along the piston and disposed between the cover portion of the needle deployment device and a proximal end of the catch; and
   the needle deployment device further comprises a return spring disposed on a distal end of the catch.

5. The device according to claim 4, wherein the release lever is rotatably coupled to the cover portion of the needle deployment device.

6. The device according to claim 5, wherein the piston is movable in a proximal direction to compress the compression spring against the cover and body portion, such that the catch is releasably held by the lever and the needle control mechanism is locked in the first position within the tubular sheath.

7. The device according to claim 6, wherein the piston is releasable in response to actuating of the release lever such that compressive force of the compression spring moves the piston distally along the longitudinal axis to extend the needle distally of the tubular sheath to the unlocked second position.

8. The device according to claim 7, wherein the piston is movable in the proximal direction by the return spring compressing against the distal end of the catch in response to releasing the compression spring, such that the needle is retracted back within the tubular sheath between the first position and the second position.

9. The device according to claim 1, wherein the needle control mechanism further includes a guide surrounding the tubular sheath.

10. The device according to claim 9, wherein the guide includes a slot configured to receive a slide surrounding the tubular sheath, the slide extending from a distal end of a needle deployment device, wherein the slide is movable along the longitudinal axis relative to the guide.

11. The device according to claim 10, wherein the slide includes one or more protrusions to catch corresponding protrusions on the guide, thereby registering the slide within the guide at predetermined locations along the guide.

12. The device according to claim 1, wherein the needle is hollow, and a guidewire is deployable therethrough.

13. The device according to claim 1, wherein the distal end of the tubular sheath includes a beveled edge, a chamfered edge, a fillet, or a groove.

14. The device according to claim 1, wherein the needle includes one or more slits in an outer perimeter of the needle.

15. The device according to claim 1, wherein the needle control mechanism is configured to automatically retract into a position retracted within the tubular sheath.

16. A system for accessing tissue, the system comprising:
a puncture device comprising:
a tubular sheath extending along a longitudinal axis, the tubular sheath having a proximal end and a distal end;
a needle disposed coaxially in the tubular sheath, the needle having a proximal end and a distal end and being movable along the longitudinal axis of the tubular sheath;
a needle control mechanism configured to hold the distal end of the needle in a first position retracted within the distal end of the tubular sheath to compress a biasing element, and being configured to release the needle to an unlocked second position such that a biasing force of the biasing element is released to expand the biasing element to extend the distal end of the needle beyond the distal end of the tubular sheath;
a piston having a catch and movable along the longitudinal axis of the tubular sheath; and
a release lever including a latch for releasably engaging the piston catch;
wherein:
the distal end of the piston is coupled to the needle;
the piston is movable in a proximal direction to compress the biasing element; and
the piston catch is releasably held by the release lever to lock the needle control mechanism in the first position; and
a steerable catheter configured to receive the puncture device coaxially along a working channel of the catheter and orient the device into position with respect to the tissue.

17. The system according to claim 16, wherein the needle control mechanism is configured to release the needle to the unlocked second position to pierce the tissue, thereby obtaining access through the tissue.

18. The system according to claim 17, wherein the needle control mechanism is configured to automatically retract the needle back within the tubular sheath by a biasing force of the biasing element after piercing the tissue.

19. The system according to claim 16, wherein the steerable catheter includes direct vision imaging components.

20. A method for accessing tissue, the method comprising:
positioning a distal tip of a catheter for a needle deployment device including a needle to access selected tissue;
setting a needle control mechanism in a retracted position and holding the needle control mechanism in the retracted position to compress a biasing element; and
deploying the needle to access the selected tissue by releasing a latch of a release lever from engagement with a catch of a piston having a distal end coupled to the needle
to cause the biasing element to expand to cause the needle to extend distally beyond the distal tip of the catheter.

* * * * *